US012364406B2

(12) United States Patent
Margiott et al.

(10) Patent No.: US 12,364,406 B2
(45) Date of Patent: Jul. 22, 2025

(54) TEMPERATURE CONTROL OF MEDICAL DEVICE

(71) Applicant: ViOptix, Inc., Newark, CA (US)

(72) Inventors: Alex Michael Margiott, Andover, MA (US); Roger Stenerson, Sunnyvale, CA (US); Lawrence Smith, Boulder, CO (US)

(73) Assignee: ViOptix, Inc., Newark, CA (US)

( * ) Notice: Subject to any disclaimer, the term of this patent is extended or adjusted under 35 U.S.C. 154(b) by 1075 days.

(21) Appl. No.: 17/146,194

(22) Filed: Jan. 11, 2021

(65) Prior Publication Data

US 2021/0212584 A1 Jul. 15, 2021

Related U.S. Application Data

(60) Provisional application No. 62/959,795, filed on Jan. 10, 2020.

(51) Int. Cl.
*A61B 5/024* (2006.01)
*A61B 5/00* (2006.01)
(Continued)

(52) U.S. Cl.
CPC ...... *A61B 5/02427* (2013.01); *A61B 5/14552* (2013.01); *A61B 5/6826* (2013.01);
(Continued)

(58) Field of Classification Search
CPC ............ A61B 5/02427; A61B 5/14552; A61B 5/6826; A61B 5/6838; A61B 2560/0276;
(Continued)

(56) References Cited

U.S. PATENT DOCUMENTS 9,282,924 B2 * 3/2016 Lin ................ A61B 5/14551
9,398,870 B2    7/2016 Bechtel et al.
(Continued)

FOREIGN PATENT DOCUMENTS

CN    102885629 A    1/2013
CN    104768461 A    7/2015
(Continued)

OTHER PUBLICATIONS

International Search Report, PCT Application PCT/US2021/013002, May 11, 2021, 6 pages.

*Primary Examiner* — Devin B Henson
(74) *Attorney, Agent, or Firm* — Aka Chan LLP

(57) ABSTRACT

A method includes increasing or decreasing a temperature of an oximeter device by cycling oximetry measurements and temperature adjustment at a predetermined frequency. During temperature adjustment, power supplied to LEDs of the oximeter device may be modulated to heat or cool the oximeter device if the oximetry device is above a temperature setpoint or below the temperature setpoint. After the device is heated to the temperature setpoint an oximetry measurement is made using the LED to illuminate patient tissue, detected the light from the tissue after illumination, and determining oximetry information for the tissue. Using the LED for heating and oximetry measurements reduces electronic components of the device improves reliability from the reduction of electronic components. The device can also not power the LEDs to allow the device to cool if the temperature is above the temperature setpoint.

43 Claims, 24 Drawing Sheets

(51) Int. Cl.
*A61B 5/1455* (2006.01)
*G07C 3/00* (2006.01)

(52) U.S. Cl.
CPC .............. *A61B 5/6838* (2013.01); *G07C 3/00* (2013.01); *A61B 2560/0276* (2013.01); *A61B 2560/028* (2013.01); *A61B 2562/08* (2013.01)

(58) Field of Classification Search
CPC ...... A61B 2560/028; A61B 2560/0238; A61B 2560/0252
See application file for complete search history.

(56) References Cited

U.S. PATENT DOCUMENTS

| | | |
|---|---|---|
| 2003/0060818 A1 | 3/2003 | Kannenberg et al. |
| 2008/0015424 A1 | 1/2008 | Bernreuter |
| 2008/0319290 A1 | 12/2008 | Mao et al. |
| 2011/0205535 A1 | 8/2011 | Soller et al. |
| 2013/0279648 A1 | 10/2013 | Joshi et al. |
| 2016/0367173 A1* | 12/2016 | Dalvi .................. A61B 5/0075 |

FOREIGN PATENT DOCUMENTS

| | | |
|---|---|---|
| WO | WO2011008382 | 1/2011 |
| WO | WO2014026200 | 2/2014 |

* cited by examiner

TEMPERATURE CONTROL OF MEDICAL DEVICE

A portion of the disclosure of this patent document contains material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

CROSS-REFERENCE TO RELATED APPLICATIONS

This application claims the benefit of U.S. patent application 62/959,795, filed Jan. 10, 2020. This application is incorporated by reference along with all other references cited in these applications.

BACKGROUND OF THE INVENTION

The present invention relates generally to optical systems that monitor parameters related to oxygen levels in tissue. More specifically, the present invention relates to optical probes, such as compact, handheld oximeters, and sheaths for the optical probes that shield the optical probes from contaminants during use and communicate status information to the optical probes regarding contaminant protection so that the optical probes are reusable.

Oximeters are medical devices used to measure the oxygen saturation of tissue in humans and living things for various purposes. For example, oximeters are used for medical and diagnostic purposes in hospitals and other medical facilities (e.g., operating rooms for surgery, recovery room for patient monitoring, or ambulance or other mobile monitoring for, e.g., hypoxia); sports and athletic purposes at a sports arena (e.g., professional athlete monitoring); personal or at-home monitoring of individuals (e.g., general health monitoring, or person training for a marathon); and veterinary purposes (e.g., animal monitoring).

In particular, assessing a patient's oxygen saturation, at both the regional and local level, is important as it is an indicator of the state of the patient's health. Thus, oximeters are often used in clinical settings, such as during surgery and recovery, where it can be suspected that the patient's tissue oxygenation state is unstable. For example, during surgery, oximeters should be able to quickly deliver accurate oxygen saturation measurements under a variety of non-ideal conditions.

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make oxygen saturation measurements of a tissue flap that has been disconnected from a blood supply. Tissue oximeters can measure oxygen levels in human tissue by exploiting these light-absorption differences.

Human tissue, as an example, includes a variety of light-absorbing molecules. Such chromophores include oxygenated hemoglobin, deoxygenated hemoglobin, melanin, water, lipid, and cytochrome. Oxygenated and deoxygenated hemoglobins are the dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving the reuse of oximeters; reducing or eliminating contamination during use; improving remote communication; improving measurement accuracy; reducing measurement time; lowering cost through reuse; reducing size, weight, or form factor; reducing power consumption; and for other reasons, and any combination of these.

Therefore, there is a need for improved tissue oximetry devices and methods of shielding oximetry devices during use for reuse of the devices.

BRIEF SUMMARY OF THE INVENTION

Embodiments relate to compact, handheld oximeters and sheaths that house and shield the handheld oximeters from patient contact and contaminants during use and shield patients from contaminants on the handheld oximeters. Because a handheld oximeter is located in a sheath and cannot contaminate patient tissue, the handheld oximeter can be reused.

A method includes increasing or decreasing a temperature of an oximeter device by cycling oximetry measurements and temperature adjustment at a predetermined frequency. During temperature adjustment, power supplied to LEDs of the oximeter device may be modulated to heat or cool the oximeter device if the oximetry device is above a temperature setpoint or below the temperature setpoint. The modulated power signal supplied to the LEDs for heating may cause the LEDs to emit an increased amount of light that provides heating or may cause the LEDs to emit less light or no light that provides cooling. In an implementation, the modulated power signal is a sine wave signal. After the device is heated to the temperature setpoint an oximetry measurement is made using the LED to illuminate patient tissue, detected the light from the tissue after illumination, and determining oximetry information for the tissue. Using the LED for heating and oximetry measurements reduces electronic components of the device improves reliability from the reduction of electronic components. The device can also not power the LEDs to allow the device to cool if the temperature is above the temperature setpoint.

The handheld oximeters implementations are entirely self-contained, without any need to connect, via wires or wirelessly, to a separate system unit for making oximetry measurements. The sources and detectors of the oximetry device are arranged in an arrangement having various source-detector pair distances that allow for robust calibration, self-correction, and spatially-resolved spectroscopy in a compact probe. Other source-detector arrangements are also possible.

In an implementation, the handheld oximeter is a tissue oximeter that can measure oxygen saturation without requiring a pulse or heartbeat. A tissue oximeter of the invention is applicable to many areas of medicine and surgery, including plastic surgery. The tissue oximeter can make oxygen saturation measurements of tissue where there is no pulse; such tissue, for example, may have been separated from the body (e.g., a flap) and will be transplanted to another place in the body.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
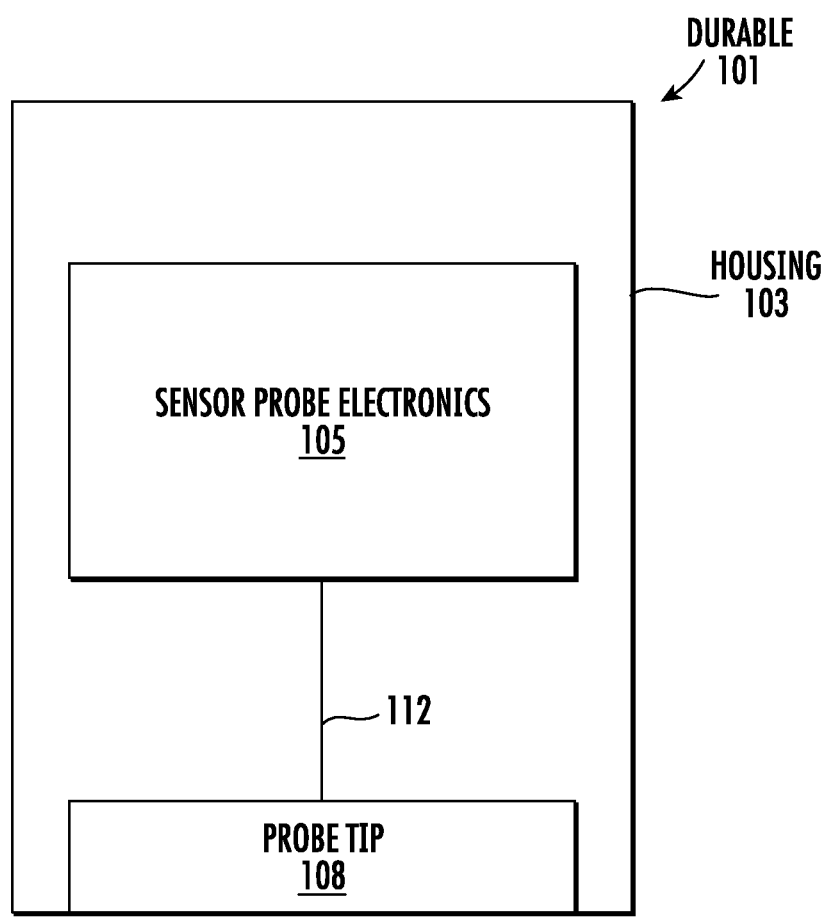
FIG. 1 shows a block diagram of a system unit for measuring various oximetry parameters of patient tissue.

Spectroscopy has been used for noninvasive measurements of various physiological properties in animal and human subjects. Visible (e.g., red light, green light, or both) and near-infrared spectroscopy is often utilized because physiological tissues have relatively low scattering in these spectral ranges. Human tissues, for example, include numerous light-absorbing chromophores, such as oxygenated hemoglobin, deoxygenated hemoglobin, melanin, water, lipid, and cytochrome. The hemoglobins are the dominant chromophores in tissue for much of the visible and near-infrared spectral range and via light absorption, contribute to the color of human tissues. In the visible and near-infrared range, oxygenated and deoxygenated hemoglobins have significantly different absorption features. Accordingly, visible and near-infrared spectroscopy has been applied to exploit these different absorption features for measuring oxygen levels in physiological media, such as tissue hemoglobin oxygen saturation (sometimes referred to as oxygen saturation) and total hemoglobin concentrations.

Various techniques have been developed for visible and near-infrared spectroscopy, such as time-resolved spectroscopy (TRS), frequency-domain techniques such as phase modulation spectroscopy (PMS), and continuous wave spectroscopy (CWS). In a homogeneous and semi-infinite model of physiological media, both TRS and PMS have been used to obtain the absorption coefficients and the reduced scattering coefficients of the physiological medium by use of the photon diffusion approximation, Monte Carlo models, or other techniques. From the absorption coefficients at multiple wavelengths, concentrations of oxygenated and deoxygenated hemoglobins can be determined and from these concentrations, the tissue oxygen saturation can be calculated.

Spatially-resolved spectroscopy (SRS) is one type of visible and near-infrared spectroscopy that allows tissue absorption to be determined independently from tissue scattering, thereby allowing absolute measurements of chromophore concentrations, such as oxygenated and deoxygenated hemoglobins. More specifically, an SRS instrument may emit light into tissue through a light source and collect the diffusely reflected light at two or more detectors positioned at different distances from the light source.

Alternatively, an SRS instrument may emit light from two or more light sources positioned at different distances from one or more detectors. Scattering of light back to the detectors is caused by relative changes of the index of refraction of the tissue and includes Mie scattering from larger structures such as mitochondria (the majority of tissue scattering is a result of mitochondria) and Rayleigh scattering from smaller structures such as intracellular vesicles. Absorption of light is caused by interaction with the tissue's chromophores.

From the reflectance (i.e., the recovered light intensity), which is recovered as a function of distance (e.g., multiple discrete distances of light detectors) from the light source, an SRS instrument can quantify the absorption coefficient and the scattering coefficient of the tissue at a single wavelength.

Multiple wavelengths of light can then be used with SRS to determine oxygenated and deoxygenated hemoglobin concentrations, and therefore, oxygen saturation within the volume of the tissue probed. Further, the wavelengths of the light source or light sources and the relative positions of the light source(s) with respect to a single detector or multiple ones of the detectors, allow tissue oximetry measurements to be made for a predetermined tissue depth. In an embodiment, one or more of the light sources and one or more of the detector source may emit and detect light so that oximetry measurements may be made for one or more predetermined tissue depths.

One field in which visible and near-infrared spectroscopy, such as SRS, is useful is in tissue flap surgery in which a tissue flap is moved from one location on a patient to another location for reconstructive surgery. Visible and near-infrared spectroscopy techniques can be used to measure oxygen saturation in a tissue flap so that the viability of the tissue flap can be determined in surgery and after surgery. Intraoperative tissue flap oximetry probes that employ visible and near-infrared SRS should be able to quickly deliver accurate oxygen saturation measurements under a variety of non-ideal conditions.

Oximetry probes adapted for SRS and other spectroscopies can come into contact with tissue, other surfaces, fluids (both liquid and gas), or other elements that can contaminate the probes. An oximetry probe that contacts tissue, for example, can be contaminated by the tissue, bacteria on the tissue, viruses on the tissue, tissue fluid, debris on the tissue, the environment near the tissue, any one of these substances, other substances, or any combination of these substances. A sheath can shield an oximetry probe from contaminants, but the efficacy of a sheath can be compromised in a number of ways. The ways in which a sheath can be compromised, allowing an oximetry probe to be contaminated, can be known and unknown. For example, a sheath housing an oximetry device may open and allow contaminants to contact the oximetry probe. The sheath opening may be relatively small and not detectable by visual inspection and the small opening may allow contaminants to enter the sheath and contact the oximetry probe. The efficacy of a sheath can be compromised if the sheath has been previously used and the previous use is unknown. The efficacy of a sheath can also be compromised if the sheath is provided from an unknown source and the sterility or sanitation of the sheath is unknown. Either inside or outside surfaces of the sheath, or both, can be contaminated if the sheath is provided by an unknown source. If the previous use of a sheath is unknown and the sheath is reused, contaminants on the sheath from an initial use can be spread during subsequent use of the sheath. Sheaths and the oximetry probes in the sheath may be contaminated in a variety of other ways. Reuse of an oximetry probe after contamination may be precluded or may increase the cost of reuse due to the cost of sanitizing or sterilizing the oximetry probe. Oximetry probes and sheaths of the present invention are directed toward improved sanitation, sterilization, or both.

FIG. 1 shows a system unit 101 for measuring various parameters of tissue in a patient. System unit 101 is sometimes referred to as a durable system unit because the unit is reusable, such as when the unit is used in combination with a protective sheath. The parameters of the tissue measured by the system unit may include an oxygen saturation level (relative oxygen saturation, absolute oxygen saturation, or both), a total hemoglobin concentration, an oxygenated hemoglobin concentration, an deoxygenated hemoglobin concentration, blood flow, pulse rate, a signal level of light reflected from the tissue, melanin concentration of tissue, other tissue parameters, or any combination of the parameters. The system unit includes housing 103, sensor probe electronics 105, and a probe tip 108, which is connected to the sensor probe electronics via a wired connection 112. Connection 112 may be an electrical connection, an optical connection, or another wired connection including any number of wires (e.g., one, two, three, four, five, six, or more wires or optical fibers), or any combination of these or other types of connections. In other implementations, connection 112 may be a wireless connection, such as via a radio frequency (RF) or infrared (IR) connection. Typically, the system unit is used by placing the probe tip in contact or close proximity to tissue (e.g., skin or internal organ or other tissue) at a site where tissue parameter measurements are desired. The system unit causes an input signal to be emitted by the probe tip into the tissue (e.g., human tissue). There may be multiple input signals, and these signals may have varying or different wavelengths of electromagnetic radiation. The input signal is transmitted into the tissue and reflected from the tissue, absorbed by the tissue, or transmitted through the tissue.

Then, after transmission through the tissue or reflection from the tissue, the signal is received at the probe tip. This received signal is received and analyzed by the sensor probe electronics. Based on the received signal, the sensor probe electronics determine various parameters of the tissue, such as an oxygen saturation level, a total hemoglobin concentration, an oxygenated hemoglobin concentration, an deoxygenated hemoglobin concentration, a blood flow, a pulse, a signal level of light reflected from the tissue, melanin concentration of tissue, or other tissue parameters. One or any combination of these parameters can be displayed on a display screen of the system unit.

In an implementation, the system unit is a tissue oximeter, which can measure oxygen saturation and hemoglobin concentration, without requiring a pulse or heartbeat. A tissue oximeter of the invention is applicable to many areas of medicine, surgery (including plastic surgery and spinal surgery), post-surgery, athlete monitoring, and other uses. The tissue oximeter can make oxygen saturation and hemoglobin concentration measurements of tissue where there is no pulse, such as tissue that has been separated from the body (e.g., a tissue flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbance of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. There are various implementations of systems and techniques for measuring oxygen saturation, such as discussed in U.S. patent applications 62/959,757, 62/959,764, 62/959,778, 62/959,787, and 62/959,808, filed Jan. 10, 2020; Ser. No. 17/146,176, 17/146,182, 17/146,186, 17/146,190, 17/146,197, and 17/146,201, filed Jan. 11, 2021; and Ser. No. 29/720,112, 29/720,115, 29/720,120, and 29/720,122, filed Jan. 9, 2020. These patent applications are incorporated by reference along with all other references cited in these applications.

Figure 2:
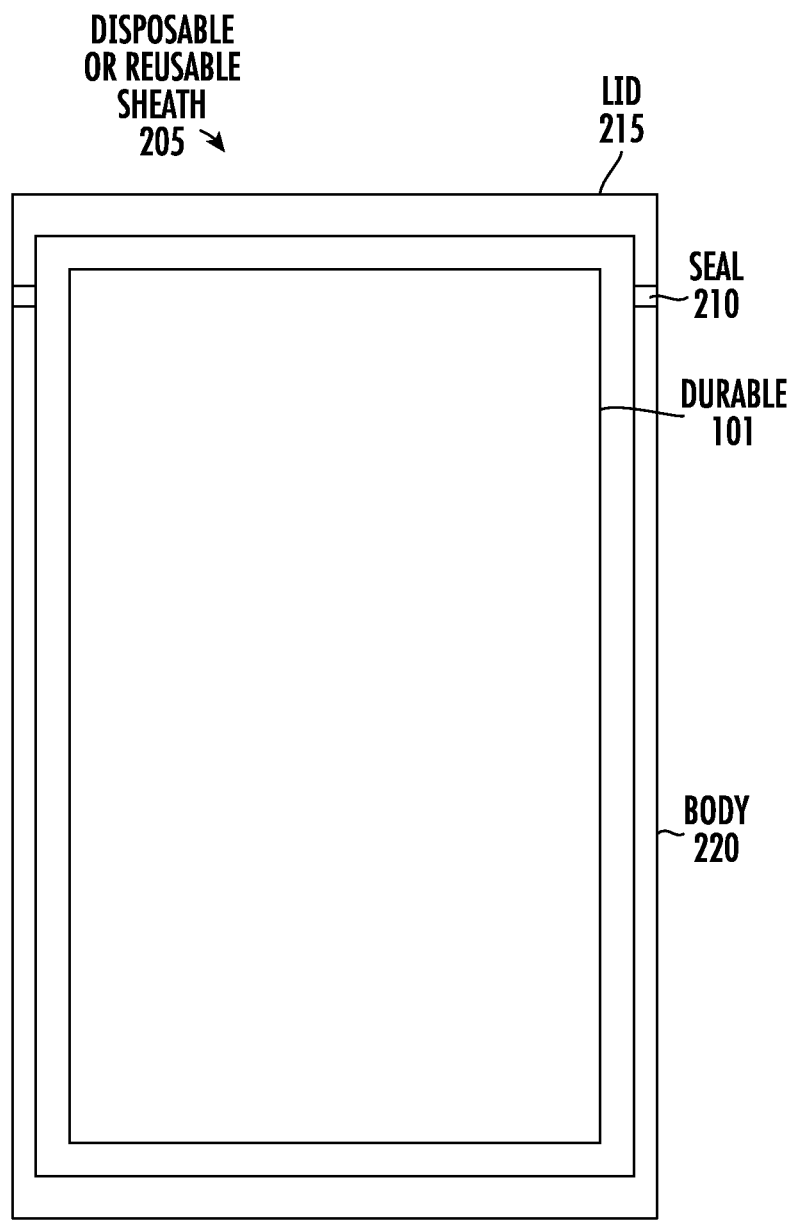
FIG. 2 shows a block diagram of the system unit housed in a sheath.

FIG. 2 shows system unit 101 housed in a sheath 205. The sheath includes a lid 215 and a body 220, which may be sealed to the lid via a seal 210. The lib may be separable from the body or may be connected to the body, such as via a hinge. The hinge may allow the lid to rotate to seal the lid to the body. The sheath may be a disposable sheath or a sheath that is reusable. For example, the system unit and sheath may travel with a patient from surgery (e.g., use) to post-surgery (e.g., reuse) for tissue monitoring.

With the lid opened, the system unit may be inserted into the sheath, and thereafter the lid may be sealed to the body to house and seal the system unit in the sheath. The system unit may then be used to make tissue parameter measurements in the sealed environment provided by the sheath. The sheath can protect the system unit from contacting elements that the sheath contacts, such as tissue, tissue fluid, biological agents (e.g., bacteria, viruses, prions, and pyrogens), debris, and other contaminants. When the lid is open and the seal is broken, the system unit may be removed from the sheath. Because the system unit is sealed into the sheath by the body, lid, and seal, the system unit can remain relatively clean, sanitized, or sterile for reuse.

Figure 3:
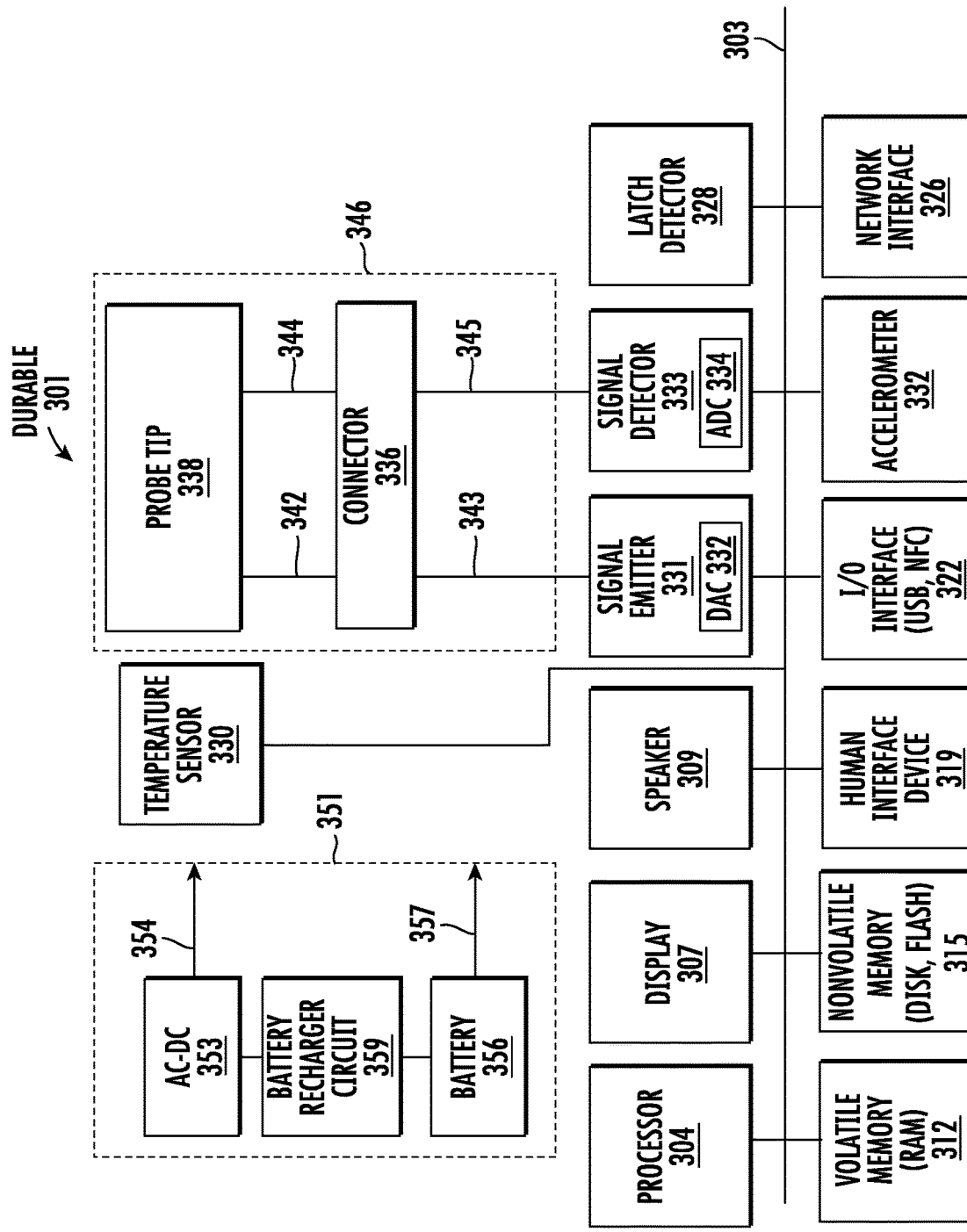
FIG. 3 shows a block diagram of the system unit, in an implementation.

FIG. 3 shows a block diagram of system unit 301, in an implementation. The system unit includes a processor 304, display 307, speaker 309, signal emitter 331, signal detector 333, volatile memory 312, nonvolatile memory 315, human interface device (HID) 319, input-output (I/O) interface 322, network interface 326, latch detector 328, temperature sensor 330, and accelerometer 332. The signal emitter may include a digital-to-analog converter 332 that converts digital signals received from the processor to analog signals that provide power to the light sources (e.g., LEDs) of the signal emitter. The signal detector may include an analog-to-digital converter 334 that converts analog generated by the detectors (e.g., photodiodes) to digital signals that are provided to the processor for processing. These components are housed within housing 103. Different implementations of the system may include any number of the components described, in any combination or configuration, and may also include other components not shown.

The components are linked together via a bus 303, which represents the system bus architecture of the system unit. Although FIG. 3 shows one bus that connects to each component of the system unit, bus 303 is illustrative of any interconnection scheme that links the components of the system unit. For example, one or more bus subsystems can interconnect one or more of the components of the system unit. Additionally, the bus subsystem may interconnect components through one or more ports, such as an audio port (e.g., a 2.5-millimeter or 3.5-millimeter audio jack port), a universal serial bus (USB) port, or other port. Components of the system unit may also be connected to the processor via direct connections, such as direct connections through a printed circuit board (PCB).

In an implementation, system unit 301 includes a sensor probe 346. The sensor probe includes a probe tip 338 and a connector 336. The probe tip is connected to the connector via a first communication link 342 and a second communication link 344. First communication link 342 may include an electrical wire, a set of electrical wires (e.g., a ribbon cable), a waveguide (e.g., a fiber optic cable), a number of waveguides (e.g., a number of fiber optic cables), a wireless communication link, or any combination of these types of links. The second communication link may include an electrical wire, a set of electrical wires (e.g., a ribbon cable), a waveguide (e.g., a fiber optic cable), a set of waveguides (e.g., a set of fiber optic cables), a wireless communication link, or any combination of these types of links. The electrical wire or sets of electrical wires of the first communication link, the second communication link, or both can include one or more electrical traces on a printed circuit board.

The connector connects (e.g., removably connects) the probe tip, the wires, waveguides, or any combination of these elements to the signal emitter and signal detector of the system unit. For example, a communication link 343 may connect the signal emitter to the connector and a communication link 345 may connect the signal detector to the connector. Each of the communication links 343 and 345 may include an electrical wire, a set of electrical wires (e.g., a ribbon cable) one waveguide, a set of waveguides, a wireless communication link, or any combination of these links. Each communication link can also include one or more electrical traces on a printed circuit board. For example, the connector may include one or more connectors that are mounted on a PCB. Communication links 342, 344, or either one of these links may be ribbon cables that connect to the probe tip and connect to connectors mounted on a PCB. In this implementation, communication links 343 and 345 can be electrical traces on the PCB that link to the single emitter, signal detector, or both. In this implementation, the signal emitters and signal detectors may be electrical emitters and detectors that control light emitters, light detectors, or both in the probe tip.

In an implementation, where the probe tip is separable from the system unit 301, connector 336 may have a locking feature, such as an insert connector that may twist or screw to lock. If so, the connector is more securely held to the system unit and it will need to be unlocked before it can be removed. This will help prevent the accidental removal of the probe tip from the system unit.

The connector may also have a first keying feature, so that the connector can only be inserted into a connector receptacle of the system unit in one or more specific orientations. This will ensure that proper connections are made.

The connector may also have a second keying feature that provides an indication to the system unit a type of probe (e.g., a probe from many different types of probes) that is attached. The system unit may be adapted to make measurements for a number of different types of probes. When a probe is inserted in the system unit, the system uses the second keying feature to determine the type of probe that is connected to the system unit. Then the system unit can perform the appropriate functions, use the appropriate algorithms, or otherwise make adjustments in its operation for the specific probe type.

In an implementation, signal emitter 331 includes one or more light sources that emit light at one or more specific wavelengths. In a specific implementation, the light sources emit five or more wavelengths of light (e.g., 730 nanometers, 760 nanometers, 810 nanometers, 845 nanometers, and 895 nanometers). Other wavelengths of light are emitted by the light sources, including shorter and longer wavelengths of light in other implementations. The signal emitter may include one or more laser diodes or one or more light emitting diodes (LEDs).

In an implementation, signal emitter 331 is an emitter that emits electrical signals to one or more light sources, which may emit light based on the received electrical signals. In some implementations, the signal emitter includes one or more light sources and electrical signal emitters that are connected to the light sources.

In an implementation, signal detector 333 includes one or more photodetectors capable of detecting the light at the wavelengths produced and emitted by the signal emitter. In another implementation, the signal detector 333 is an electrical signal detector that detects electrical signals generated by one or more photodetectors. In another implementation, the signal detector includes one or more photodetectors and one or more electrical detectors that are connected to the photodetectors.

In an implementation, HID 319 is a device that is adapted to allow a user to input commands into the system unit. The HID may include one or more buttons, one or more slider devices, one or more accelerometers, a computer mouse, a keyboard, a touch interface device (e.g., a touch interface of display 307), a voice interface device, or another HID.

In an implementation where the HID is an accelerometer and the system unit is a handheld unit, the accelerometer may detect movements (e.g., gestures) of the system unit where the system unit may be moved by a user. Movements may include a left movement, right movement, forward movement, back movement, up movement, down movement, one or more rotational movements (e.g., about one or more axes of rotation, such as the x-axis, y-axis, z-axis, or another axis), any combinations of these movements, or other movements.

Information for the various movements detected by the accelerometer may be transmitted to the processor to control one or more systems of the system unit. For example, an upward movement (e.g., a lifting movement) may be transmitted to the processor for powering on the system unit. Alternatively, if the system unit is set down and left unmoved for a predetermined period of time, then the processor may interpret the lack of movement detected by the accelerometer as a standby mode signal and may place the system unit in a standby power mode (a lower power mode than a normal operation mode where oximetry measurements can be made by the system unit), or a power-down signal and may power down the system unit.

When the system unit is powered on, information for a left movement or a right movement detected by the accelerometer and transmitted to the processor may be used by the processor to control the system unit. For example, a left or right movement of the system unit may be used by the processor to change menu items displayed on the display. For example, the processor may use the information for a left movement to scroll menu items on the display to the left (e.g., scroll a first menu item left and off of the display to display a second menu item on the display). The processor may use the information for a right movement of the system unit to scroll menu items to the right (e.g., scroll a first menu item right and off of the display, and display a second menu item on the display).

The HID and processor may be adapted to detect and use various movements to activate a menu item that is displayed on the display. For example, information for an upward movement or a downward movement may be detected and used to activate a menu item that is displayed on the display. For example, if a user is prepared to take an oximeter measurement and a menu option is displayed for taking an oximeter measurement, a quick downward movement of the system unit may start a measurement when the probe tip is placed in contact with tissue.

The HID may include one or more accelerometers to detect motion in various directions (e.g., linear, rotational, or both). The accelerometers can include one or more capacitive micro-electro-mechanical system (MEMS) devices, one or more piezoresistive devices, one or more piezoelectric devices, or any combination of these devices.

In an embodiment, accelerometer 332 is adapted to detect relatively high G-force accelerations associated with a shock that the system unit experiences. The shock may be from bumping the system into something, dropping the system unit (e.g., dropping the system unit on a table or the floor), or other shock events. In an implementation, if the accelerometer indicates to the processor that a shock event has occurred, the processor can take a number of actions. For example, the processor can shut down the system unit. The processor can display one or more messages on the display. The messages may indicate that the system unit should be recalibrated. The message may indicate that contact between the system unit and the sheath should be checked. The accelerometer may include one or more capacitive micro-electro-mechanical system (MEMS) devices, one or more piezoresistive devices, one or more piezoelectric devices, or any combination of these devices.

In an implementation, the latch detector 328 is adapted to detect whether a latch of the sheath is latched or unlatched. If the latch is latched, then the system unit is housed and enclosed in the sheath. In this configuration, with the system unit housed and enclosed in the sheath, the system unit may not be contaminated by material contacting the outside surface of the sheath. If the latch is unlatched and the system unit is in the sheath, then the system unit might be contaminated with material contacting the outside surface of the sheath. That is, the seal that seals the lid of the sheath to the body of the sheath may be unsealed (i.e., opened) and contaminates may pass from outside of the sheath to the inside of the sheath where the system unit is located.

In an implementation, at least a first portion of the latch is metal. Other portions of the latch may be metal or other material, such as a plastic material. The first portion of the latch is a first distance from the latch detector when the latch is latched and is a second distance from the latch detector when the latch is unlatched. The first distance is less than the second distance.

In an implementation, the latch detector includes an inductor that can inductively couple to the first portion of the latch. The inductor can be driven with a direct current or an alternating current and thus detect when the first portion of the latch moves toward the latch detector or away from the latch detector. The latch detector can be calibrated so that the latch detector can detect when the latch moves to the first distance away from the latch detector or farther than the first distance away from the latch detector. The latch detector can include an analog-to-digital converter, a digital signal processor (DSP), or both that digitize and analyze the current flowing through the inductor. One or both of these circuits can communicate the digitalized information to the processor that can determine whether the latch is open or closed. The processor can display a message on the display to indicate whether the latch is open or closed, whether the seal for the sheath is sealed or unsealed, warn of potential contamination, or other messages associated with the latch being opened or closed.

In an embodiment, the latch detector is a capacitive detector that can capacitively couple to the latch. The capacitive detector can detect the latch in the latched position at a first distance from the capacitive detector and moving away from the latched position and the first distance.

The nonvolatile memory 315 may include a FLASH memory, other nonvolatile solid-state storage (e.g., USB flash drive), battery-backed-up volatile memory, tape storage, reader, and other similar media, and combinations of these. In some implementations, the nonvolatile memory includes a mass disk drive, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc). The volatile memory may include a random access memory (RAM).

The processor may include a microcontroller, a microprocessor, an application specific integrated circuit (ASIC), programmable logic (e.g., field programmable gate array), or any combination of these circuits. The processor may include multiple processors or a multicore processor, which may permit parallel processing of information.

In an implementation, the system unit is part of a distributed system. In a distributed system, individual systems are connected to a network and are available to lend resources to another system in the network as needed. For example, a single system unit may be used to collect results from numerous sensor probes at different locations.

Aspects of the invention may include software executable code, firmware (e.g., code stored in a read only memory (ROM) chip), or both. The software executable code or firmware may embody algorithms used in making oxygen saturation measurements of the tissue. The software executable code or firmware may include code to implement a user interface by which a user uses the system, displays results on the display, selects or specifies parameters that affect the operation of the system, or execute algorithms and calculations to generate a result.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, MATLAB (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows XP, Windows XP x64 Edition, Windows Vista, Windows CE, Windows 7, Windows 8, Windows 10, Windows Mobile), Linux, HP-UX, UNIX, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may communicate with other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or another device (e.g., a laptop computer, smartphone, or personal digital assistant), a user accesses the system unit of the invention through a network such as the Internet. The user will be able to see the data being gathered by the system unit. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 4:
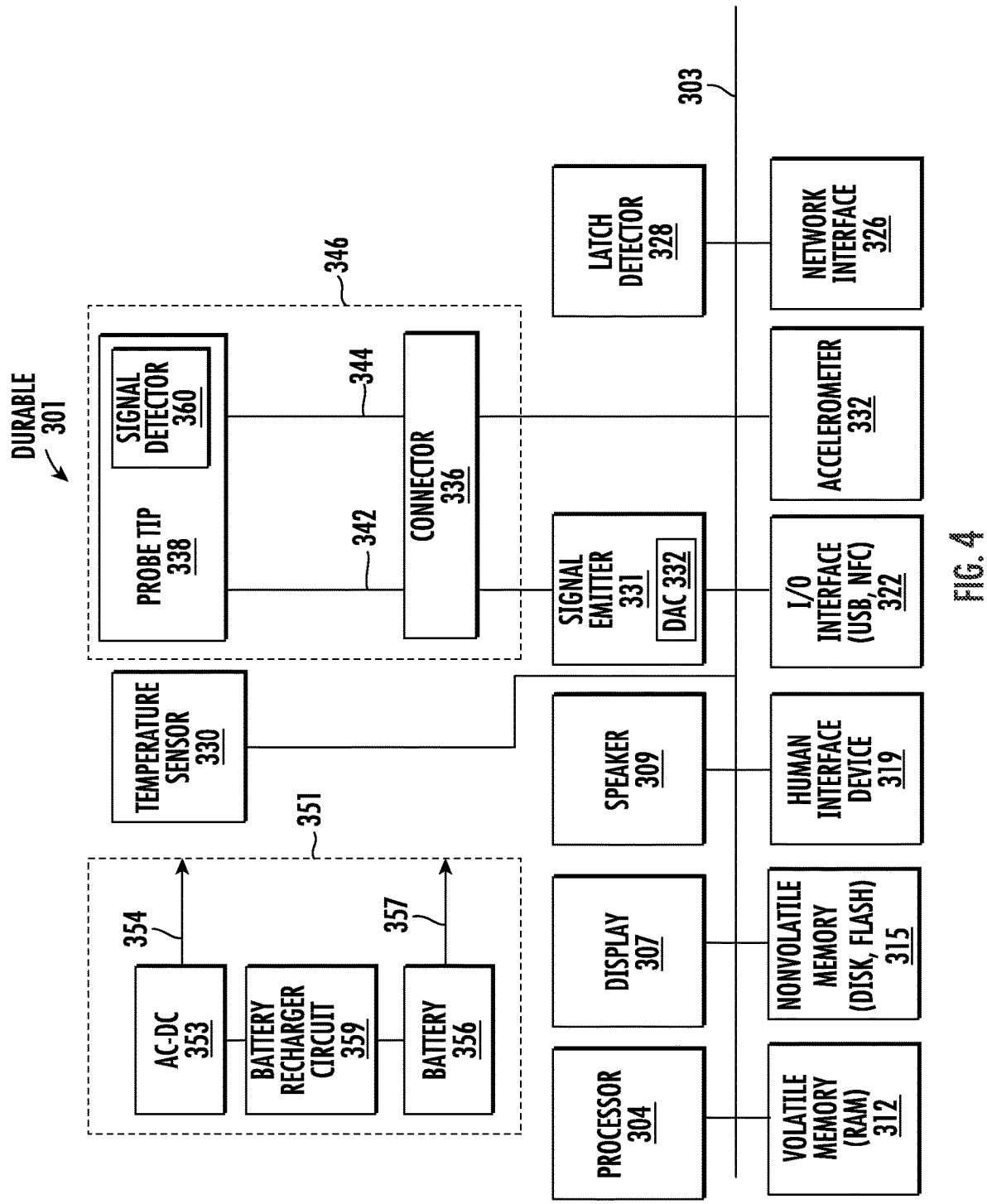
FIG. 4 shows a block diagram of the system unit, in an implementation.

FIG. 4 shows a block diagram of system unit 401, in an implementation. System unit 401 is similar to system unit 301 but differs in that the signal detector 344 is located in probe tip 346. A wire or set of wires (e.g., a ribbon cable) may connect the signal detector to the bus and processor. For example, a ribbon cable that is connected to the signal detector may also be connected to a connector or socket mounted on a PCB that the processor and other circuits are mounted on. The signal detector may be located at a probe face of the probe tip. The signal emitter may be optically located behind the probe face of the probe tip.

Figure 5:
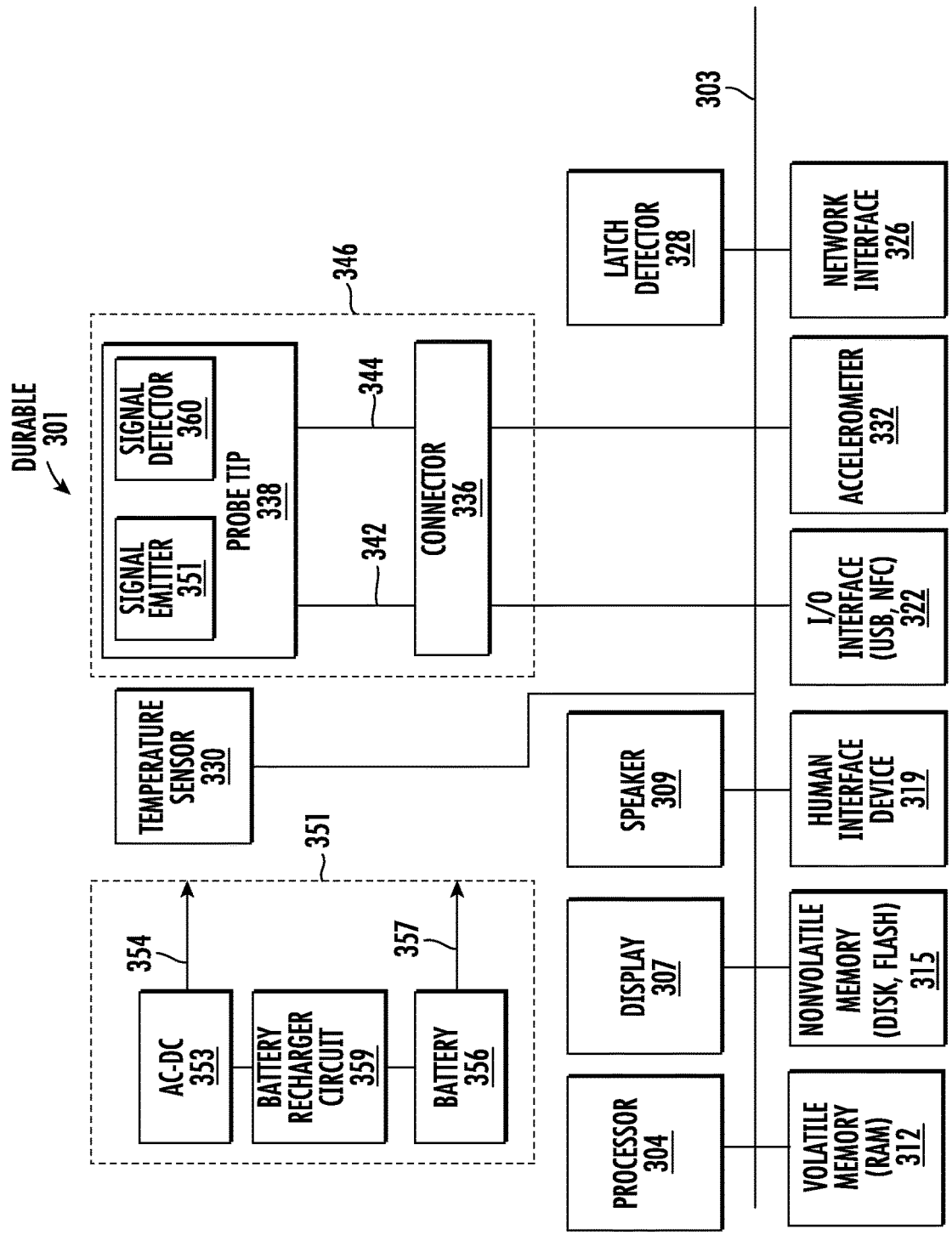
FIG. 5 shows a block diagram of the system unit, in an implementation.

FIG. 5 shows a block diagram of system unit 501, in an implementation. System unit 501 is similar to system units 301 and 401 but differs in that the signal emitter 331 and the signal detector 344 are located in probe tip 346. A wire or wires (e.g., one or more ribbon cables) may connect the signal emitter, the signal detector, or both to the bus and processor. A first ribbon cable may connect the signal emitter to the bus and processor and a second ribbon cable may connect the signal detector to the bus and processor. For example, the first ribbon cable that is connected to the signal emitter may also be connected to a connector or socket mounted on a PCB that the processor and other circuits are mounted on, and the second ribbon cable that is connected to the signal detector may also be connected to a connector or socket mounted on the PCB. The signal detector may be located at a probe face of the probe tip. The signal emitter may be optically located behind the probe face of the probe tip.

In an implementation, connector 336 includes a locking feature, such as an insert connector that inserts into a connecting port and then twists or screws to lock. If so, the connector is more securely held to the system unit and it will need to be unlocked before it can be removed. This will help prevent accidental removal of the probe.

In an implementation, connector 336 includes one or more PCBs that are connected to one or more wires (e.g., ribbon cables) that connect to the signal emitter, the signal detector, or both. For example, a first ribbon cable may connect to a first PCB that connects to the signal emitter. A second ribbon cable may connect to a second PCB that connects to the signal detector.

Block 351 shows a power block of the system unit having both AC and battery power options. In an implementation, the system includes an AC-to-DC converter 353, such as a full-wave rectifier. The converter takes AC power from a wall socket, converts AC power to DC power, and the DC output is connected (indicated by an arrow 354) to the components of the system unit needing power.

In an implementation, the system is battery operated. The DC output of a battery 356 is connected (indicated by an arrow 357) to the components of the system unit needing power. The battery may be recharged via a recharger circuit 359, which received DC power from the AC-to-DC converter. The AC-to-DC converter and recharger circuit may be combined into a single circuit. In an implementation, the battery is rechargeable via magnetic charging or induction charging.

In an implementation, block 351 is a battery module that includes one or more batteries that power the components of the system unit. The batteries may be rechargeable or disposable batteries. The block may not include the AC-to-DC converter. Block 351 may be a block that is integrated with the system unit or is separable from the system unit.

Figure 6:
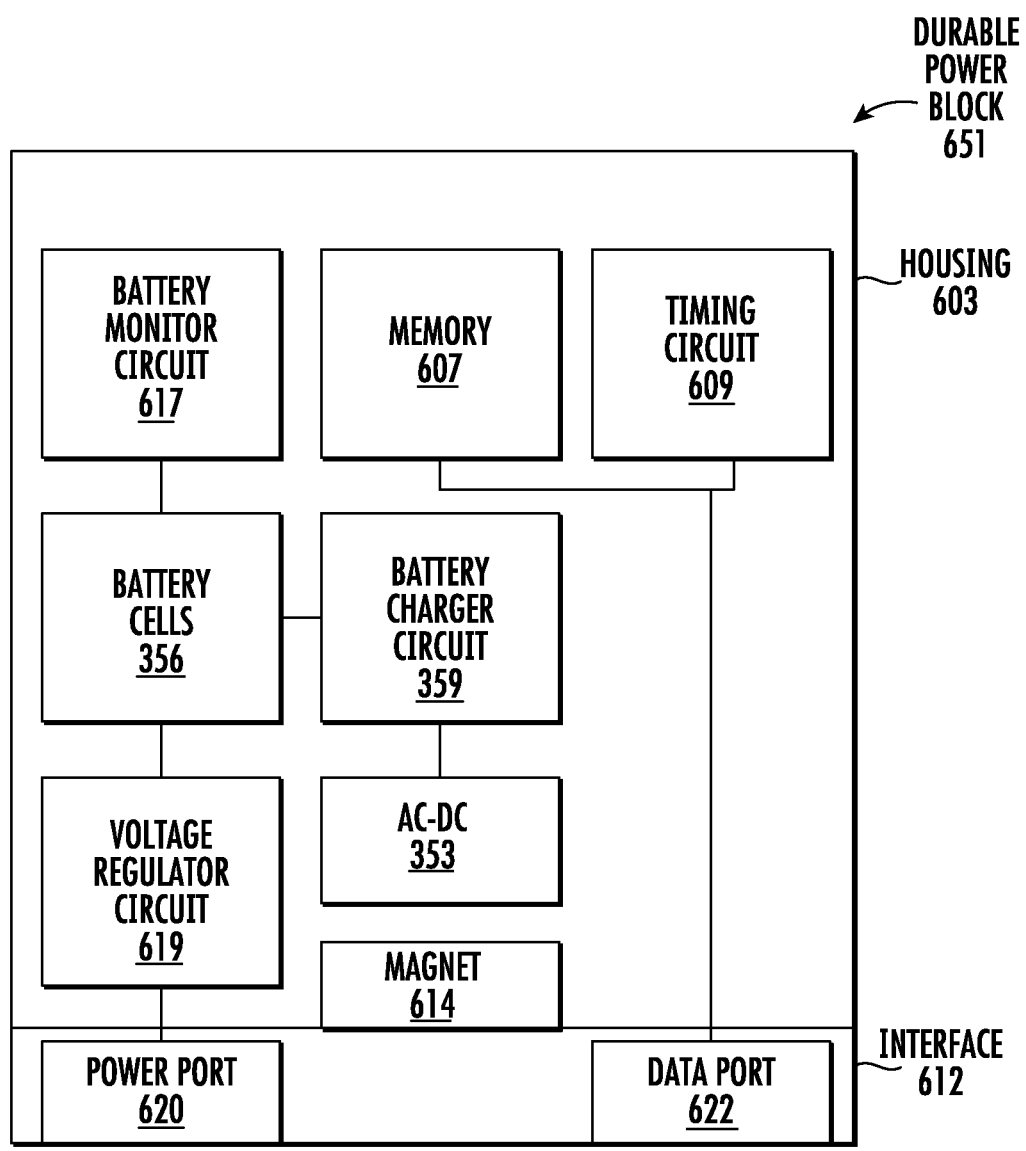
FIG. 6 shows a diagram of the power block of the system unit, in an implementation.

FIG. 6 shows block 651 that is a power block, in an implementation. Block 651 is similar to block 351 but may include a battery monitor 617, a voltage regulator circuit 619, a memory 607, a timing circuit 609, an interface 612, which includes a power port 620 and a data port 622, a magnet 614, other circuits, or any combination of these circuits.

Battery monitor 617 may be connected to the battery cells 356 and may monitor the capability of the battery cells. For example, the battery monitor may determine a current charge state, such as a percentage of the total possible charge. The battery monitor may determine the charge capacity of the battery cells. The charge capacity may be a percentage of the charge capacity compared to the charge capacity of the battery cells when new. The battery monitor may determine the maximum power delivery capability of the battery.

The battery cells may be disposable battery cells, such as alkaline battery cells, or rechargeable battery cells, such as nickel metal hydride, lithium battery cells (e.g., Li/FeS2 size AA, AAA, N, CR123, 18650, or others), lithium polymer, or other types of cells. The power back may include four battery cells that are AA size cells that output 1.5 volts. The four batteries may be in series to output 6 volts, or may be in series and parallel to output 3 volts.

Voltage regulator circuit 619 may be connected between the battery cells and the power port of the battery interface 612. The voltage regulator circuit conditions the voltage output from the battery to output an approximately constant voltage. The voltage regular circuit may also include a DC-to-DC converter that converts a first voltage output from the battery cells to a second voltage that is different from the first voltage.

The timing circuit is a circuit that determines the amount of time length that the battery has been used. Information for the amount of time may be stored in the memory and may be transferred through the data port to the processor when the processor queries the memory for the information.

In an embodiment, the memory may also store an encrypted identifier that identifies the power block. The processor may be adapted to retrieve the encrypted identifier via the power blocks data port. The processor or another decryption circuit of the system unit may decrypt the encrypted identifier and may identify the power block based on the identifier after decryption. The identifier may identify the manufacturer of the power block or may identify other information about the power block, such as the manufacturing date, the battery cell type, battery cell voltage, elapsed usage time, or any combination of these elements. In an implementation, if the identifier is not a known identifier that is known to the system unit, then the processor with not allow the system unit to operate with the power block. That is, the system unit will not operate with a power block manufactured by an unknown manufacturer. Allowing the system unit to operate with known (e.g., authorized) power blocks, the system unit is assured that the power provided by the power block is within the operating specifications of the system unit. Therefore, the circuits, signal emitters, signal detectors, and other elements of the system unit will operate within predetermined parameters and will not operate outside of the predetermined parameters. Also, using a known battery from a known manufacturer provides that the stem unit will operate for a known period of time so that the system unit will not run out of battery power during a medical procedure, such as a surgery. Operating the system unit according to predetermined parameters, facilitates the system unit making accurate and reliable oximetry measurements.

In an implementation, nonvolatile memory 315 stores one or more identifiers for one or more power blocks that may operate with the system unit. The processor may compare the identifier for the power pack that has been decrypted to the one or more identifiers retrieved from the nonvolatile memory to determine whether the power block will be allowed to operate with the system unit. If the power block is not authorized for use with the system unit, the processor may cause a message to be displayed on the display that indicates that the power block is not authorized for use with the system unit. If the power block is authorized to operate with the system unit, then the system unit may operate to make oximetry measurements without displaying information on the display about the authenticity or the inauthenticity of the power block.

In an implementation, the memory of the power block stores an indicator that indicates whether the battery has been previously used. The indicator may be the time information for the amount of time that the power block has operated. A nonzero use time stored in the memory is an indicator that the power block has been previously used. Alternatively, the indicator may be an identifier of a system unit that the power block has been connected to and provided power to. For example, the nonvolatile memory of the system unit may store an identifier of a system unit. The processor of the system unit may transfer the system identifier of the system unit to the power block for storage in the power block's memory.

When the power block is attached to a system unit, the processor of the system unit may query the power block's memory to retrieve any system identifier that may be stored in the power block's memory. In an implementation, if a system identifier retrieved from the power block's memory is different from the system identifier of the system unit that retrieved the system unit from the power block's memory, then the system unit will not operate with the power block. The implementation attempts to ensure that a power block is fully charged and can be used for the duration of a medical procedure (e.g., a surgery) without the power block running out of stored energy. Ensuring that a power block is unused prior to using the power block during a medical procedure provides that the power block will not run out of power during the procedure and minimize risk to a patient. That is, patient risk is lowered if a system unit used during a procedure does not run out of power and can be used for patient monitoring when required.

In an implementation, when the power block is attached to a system unit, the processor of the system unit may query the power block's memory to retrieve the time information for the amount of time that the power block has operated. In an implementation, if the system unit determines that the power block has been previously used based on the time information, then the system unit will not operate with the power block. Similar to the embodiment described immediately above, ensuring that a power block is unused prior to using the power block during a medical procedure provides that the power block will not run out of power during the procedure and minimize risk to a patient.

The power block may include one more magnets 614 that are arranged in an arrangement, such as a square, a rectangular, or another arrangement. A system unit may also have one or more magnets or one or more metal plates (e.g., ferromagnetic plates) that are arranged in an arrangement that is complementary to the arrangement of magnets in the power block. The magnets of the power block may attract the magnets or metal plates of the system unit when the power block is placed in contact with the system unit. The magnetic attraction between the magnets or plates may hold the power block in place when the system unit is being used.

The power block may include one more plates (e.g., ferromagnetic plates) that are arranged in an arrangement, such as square, rectangular, or another arrangement. The system unit may include one or more magnets that are arranged in a complementary arrangement. The magnets of the system unit may magnetically attract the metal plates of the power block when the power block is placed in contact with the system unit. The magnetic attraction between the magnets and plates may hold the power block in place when the system unit is being used.

In an implementation, the power port of the power block includes at least two electrical contacts (e.g., a power contact and a ground contact) and the data port includes at least two electrical contacts (e.g., a data line and a shared ground contact with the power port). The electrical contacts are arranged in an arrangement, such as in a row, in a square, in a rectangle, another arrangement. The system unit includes a power port that includes at least two electrical contacts (e.g., a power contact and a ground contact) and includes a data port that includes at least two electrical contacts (e.g., a data line and a shared ground contact with the power port). The arrangement of the electrical contacts is complementary to the electrical contacts of the power block.

When the power block is placed in contact with the system unit, the magnetic attraction between the magnets or between the magnets and metal plates forces the electrical contacts of the power port in the system unit into contact with the electrical contacts of the power port of the power block. Also, the magnetic attraction forces the electrical contacts of the data port in the system unit into contact with the electrical contacts of the data port of the power block. As such, electrical power can be transferred from the power block to the system unit to power the circuits and other elements of the system unit, and data can be transferred between the power block and the system unit.

Figure 7:
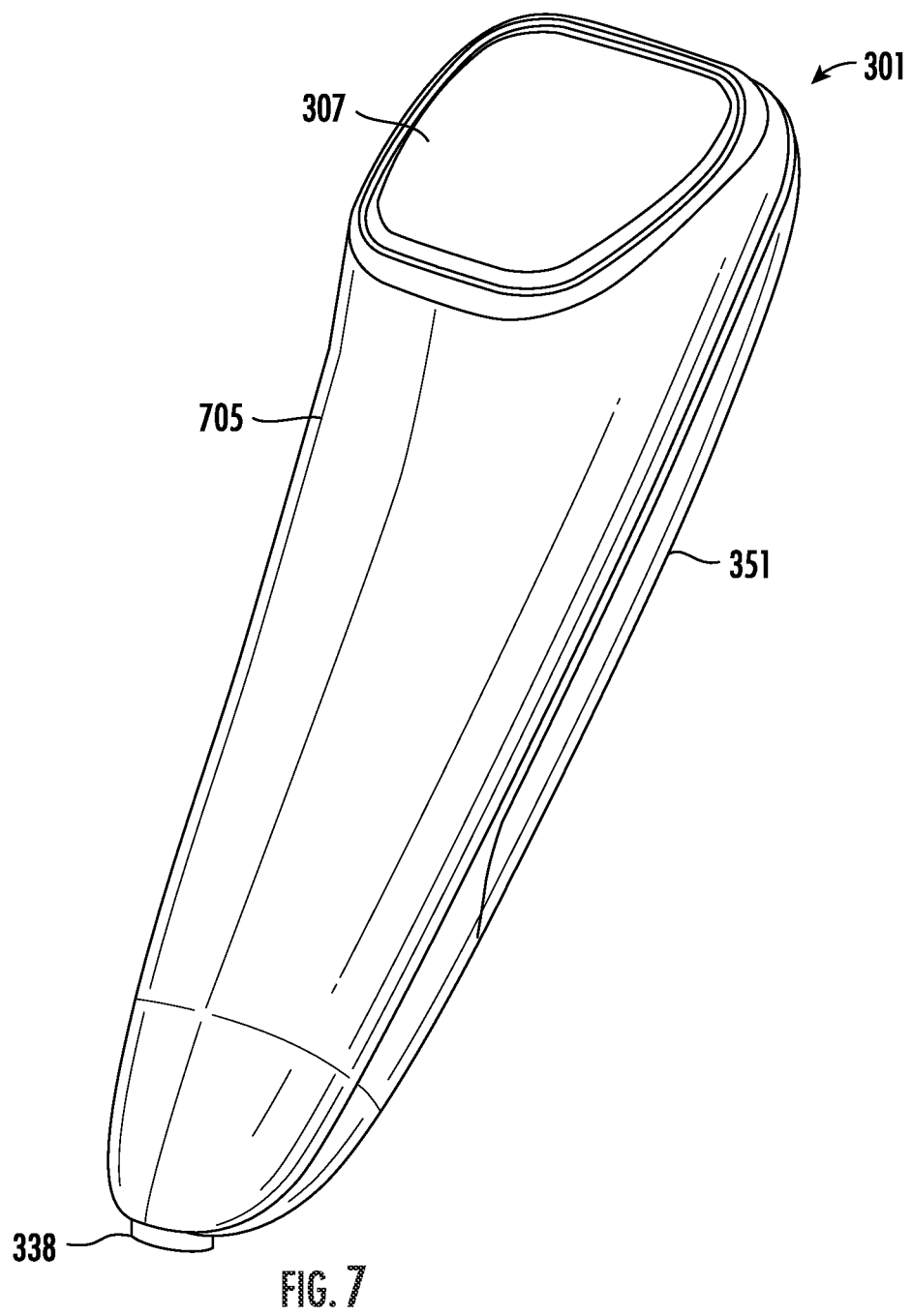
FIG. 7 shows a perspective view of the system unit and power block.

FIG. 7 shows a perspective view of the system unit 301 and power block 351 coupled to the system unit, in an implementation. The display 307 of the system unit is located at a first end of the system unit and the probe tip 338 is located at a second end of the system unit where the first and second ends of proximal and distal ends of the unit. The housing of the system unit tapers from the first end to the second end. The described circuit elements are housed in the housing 705 of the system unit. housing 705 of the system unit. When the second window of the sheath is in contact with tissue, the first window of the sheath and the display of the system unit faces away from the tissue for easy visibility of the display. In an implementation where the system unit is used without a sheath, when the probe face of the system unit is in contact with tissue, the display faces away from the tissue for easy visibility of the display.

Figure 8:
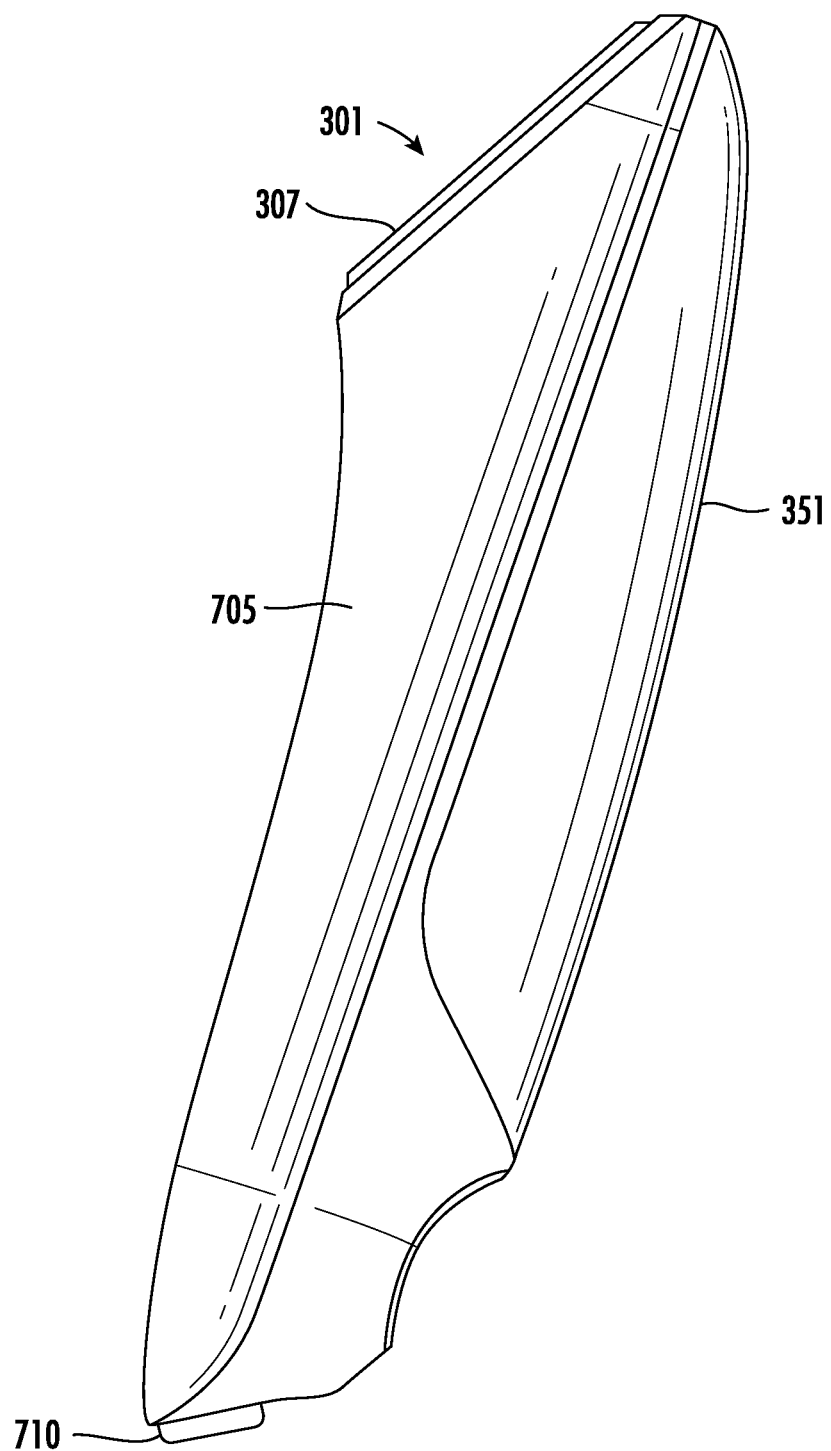
FIG. 8 shows a side view of the system unit.

FIG. 8 shows a side view system unit 301, in an implementation. The housing 705 of the system unit includes a bezel 710 that houses a portion of the probe tip. The bezel includes an opening the exposes a probe face of the probe tip.

Figure 9:
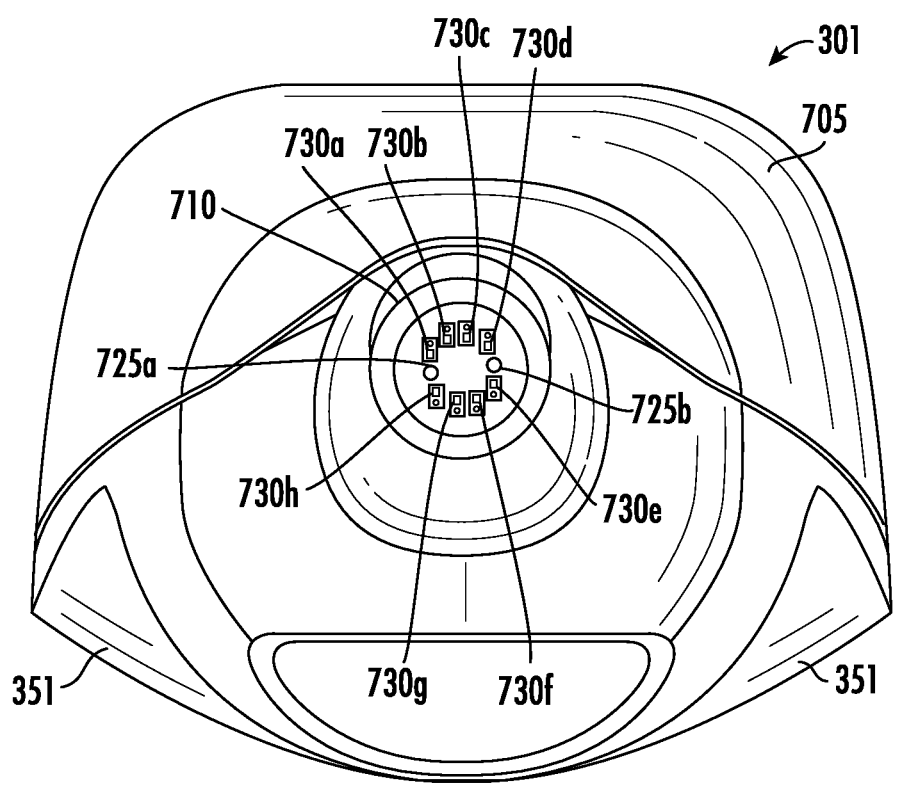
FIG. 9 shows an end view of the system unit.

FIG. 9 shows an end view of the second end of the system unit, in an implementation. The end of bezel 710 is shown with the probe face 715 in the opening of the bezel. The probe face may include an aperture plate 720 that includes a number of source apertures, for example, source apertures 725*a* and 725*b*, and includes a number of detector apertures 730*a*-730*h*. Each of the source apertures may be included in a source structure that may include light sources, such as one or more of optical fibers, laser diodes, LEDs, one or more portions of the aperture plate, or other structures at the probe tip in any combination. Each of the detector apertures may be included in a detector structure that may include light detectors, such as one or more of optical fibers, photodetectors, one or more portions of the aperture plate, or other structures at the probe tip in any combination.

Figure 10A:
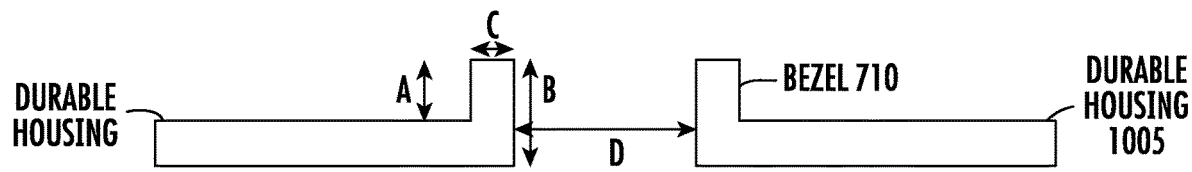
FIGS. 10A-10D show a number of steps for forming the probe face of the probe tip and forming the finished bezel of the housing of the system unit.

FIGS. 10A-10D show a number of steps for forming the probe face 715 of the probe tip 338 and forming the finished bezel 710 of the housing 1005 of the system unit 301. FIG. 10*a* shows the bezel 710 of the housing 1005 at an initial height A where the height is from the outside surface of the housing to the top of the bezel. Height A may be from about 3.5 millimeters to about 4 millimeters. In a specific implementation, height A is about 3.75 millimeters. The inner height B of the bezel is from the inside surface of the housing to the top of the bezel. Height B may be from about 4.5 millimeters to about 5.5 millimeters. In a specific implementation, height B is about 5.05 millimeters. The diameter D of the opening of the bezel may be from about 8 millimeters to about 10 millimeters. In a specific implementation, the diameter of the opening of the bezel may be about 9.1 millimeters. The width C of the bezel at the bezel's end may be about 1.0 millimeters to about 2.0 millimeters. The width C may vary around the circumference of the bezel. In a specific implementation, the width C of the bezel is about 1.5 millimeters.

Figure 10B:
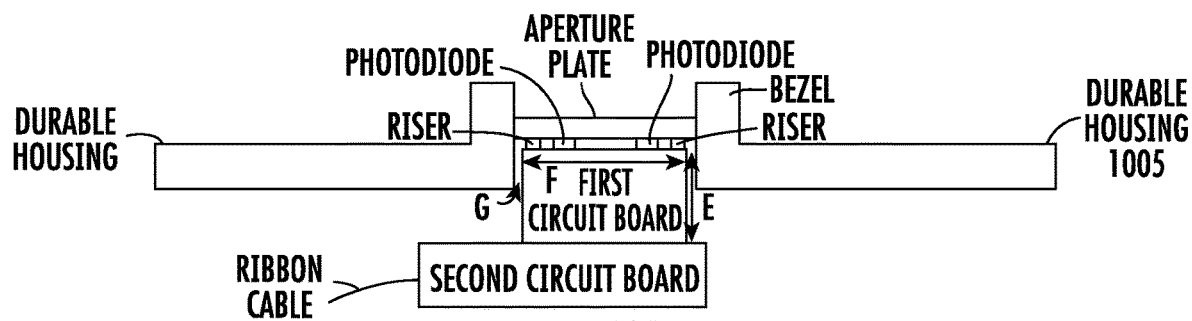

FIG. 10B shows the housing and bezel with a portion of the probe tip 338 in the housing and bezel. The portion of the probe tip shown includes a first circuit board 1020, a second circuit board 1025, riser 1030, photodiodes 1035, an aperture plate 1040, and a ribbon cable 1045 connected to the second circuit board. The first and second circuit boards may include electrical traces that are coupled. The second circuit board may be a fiberglass circuit board (e.g., FR4) that includes electrical traces that are connected to electrical traces of the first circuit board. The electrical traces of the first circuit board may extend upward from the second circuit board along the outer surface of the first circuit board. The first and second circuit boards may be connected by mechanical fasters, plastic welding, an adhesive (e.g., epoxy), another material, or any combination of these materials. The first circuit board may have a diameter F of about 6 millimeters to about 8 millimeters. In a specific implementation, the diameter F of the first circuit board is about 7 millimeters. The first circuit board may have a height E of about 3 millimeters to about 4 millimeters. In a specific implementation, the height E of the first circuit board is about 3.5 millimeters.

A distance G between the side of the first circuit board and the inner sidewall of the bezel may be about 0.5 millimeters to about 1.5 millimeters. In a specific embodiment, the distance between the side of the first circuit board and the inner sidewall of the bezel may be about 1.05 millimeters.

The riser may be connected to both the first circuit board and the aperture plate and may separate the first circuit board and aperture plate may be predetermined height. The photodiodes may be mounted on a top surface of the first circuit board and be connected to the electrical traces of the first circuit board. The aperture plate may include an aperture for each photodiode that is mounted on the first surface of the first circuit board and the diodes may respectively be inside the apertures. The height of each riser may be about 100 micrometers to about 200 micrometers. In an implementation, the height of each riser is about 150 micrometers.

Figure 10C:
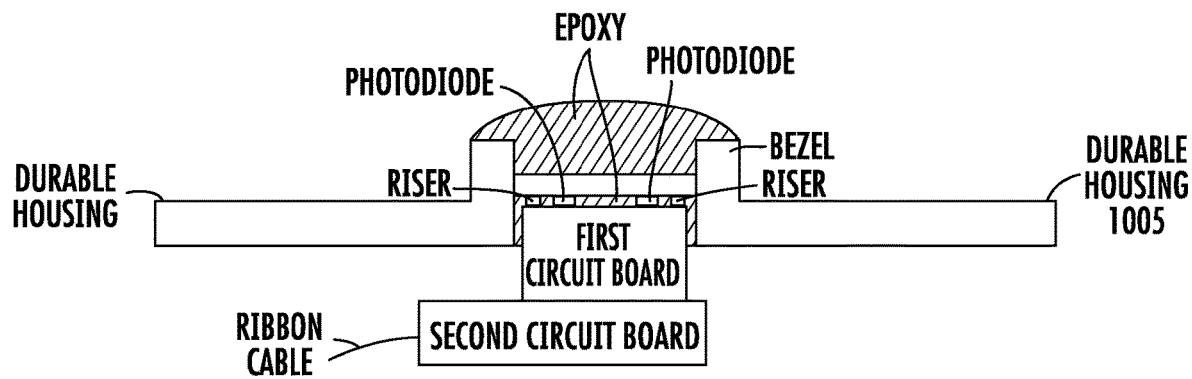

After the portion of the probe tip shown in FIG. 10B is placed into the opening of the bezel, epoxy is flowed into the opening as shown in FIG. 10C. The epoxy may flow into the apertures of the aperture plate, along the sides of the first circuit board, and may flow to the second circuit board and around the sides of the second circuit board.

Figure 10D:
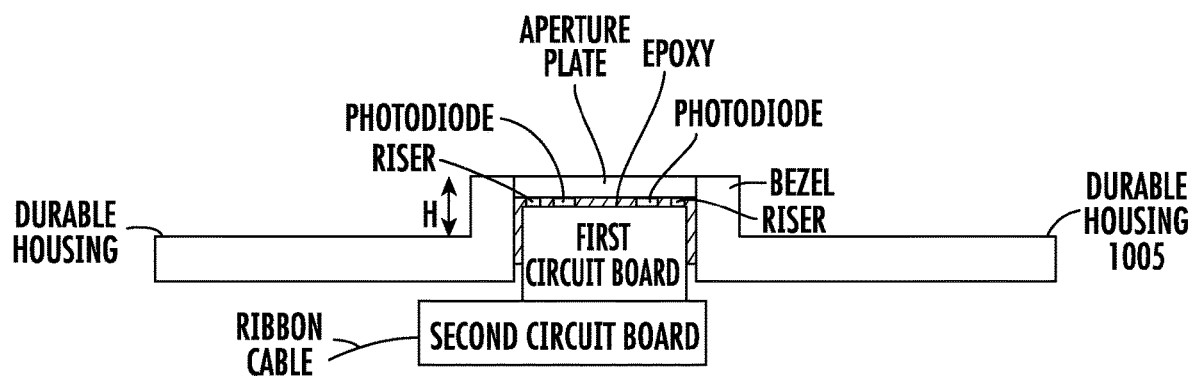

After the epoxy cures, the epoxy and a portion of the side of the bezel may be removed (e.g., polished down) to a final height, as shown in FIG. 10D. The final outside height H of the bezel may be about 2.0 millimeters to about 3 millimeters. In a specific implementation, the final outside height H of the bezel is about 2.58 millimeters. In an implementation, a portion of the aperture plate may also be thinned (e.g., polished thinner) when the bezel and epoxy are removed. The aperture plate can include a marker embedded in the plate. The embedded marker is exposed and polished away in the polishing process, the polishing is completed when the marker is polished away.

In an implementation, the epoxy is polished down to the surface of the tops of the photodetectors inside the apertures of the aperture plate. In another implementation, a thin layer of epoxy remains over the tops of the photodiodes after polishing.

Figure 11:
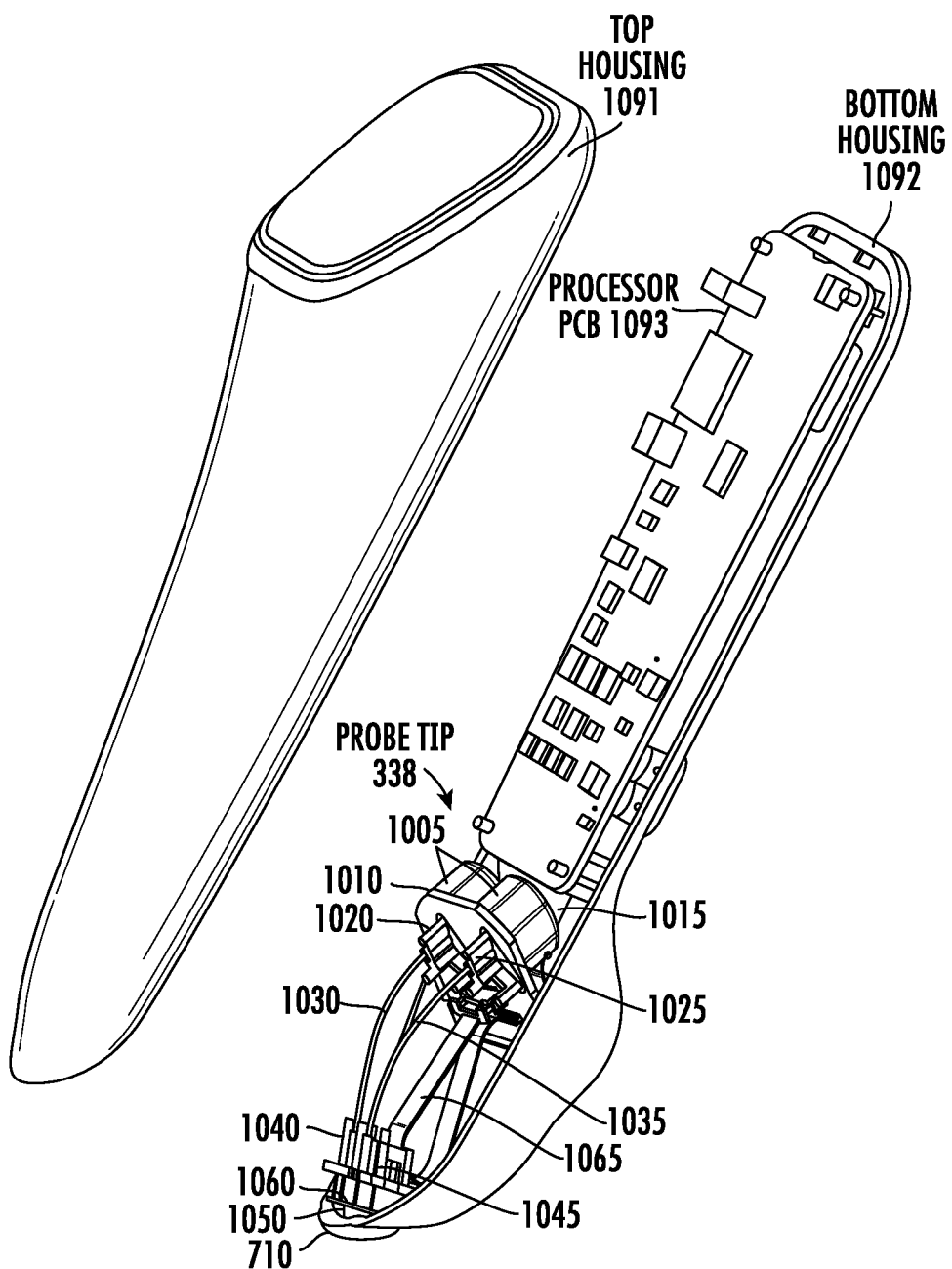
FIG. 11 shows a view of the system unit with a top housing of the system unit separated from a bottom housing of the system unit.

FIG. 11 shows a view of the system unit with a top housing 1091 of the system unit separated from a bottom housing 1092 of the system unit. This figure shows a PCB 1093 on which various circuits of the system unit are mounted, such as the processor 304, volatile memory 312, nonvolatile memory 315, human interface device (HID) 319, input-output (I/O) interface 322, network interface 326, and accelerometer 332.

The probe tip 338 is attached to a lower portion of the bottom housing. The probe tip includes two reflector domes 1005, an LED PCB 1010, a first optical fiber holder 1020, a second optical fiber holder 1025, a third optical fiber holder 1040, a fourth optical fiber holder 1045, a first optical fiber 1030, a second optical fiber 1035, a first PCB 1050, a second PCB 1060, a first ribbon cable 1015, and a second ribbon cable 1065.

Figure 12:
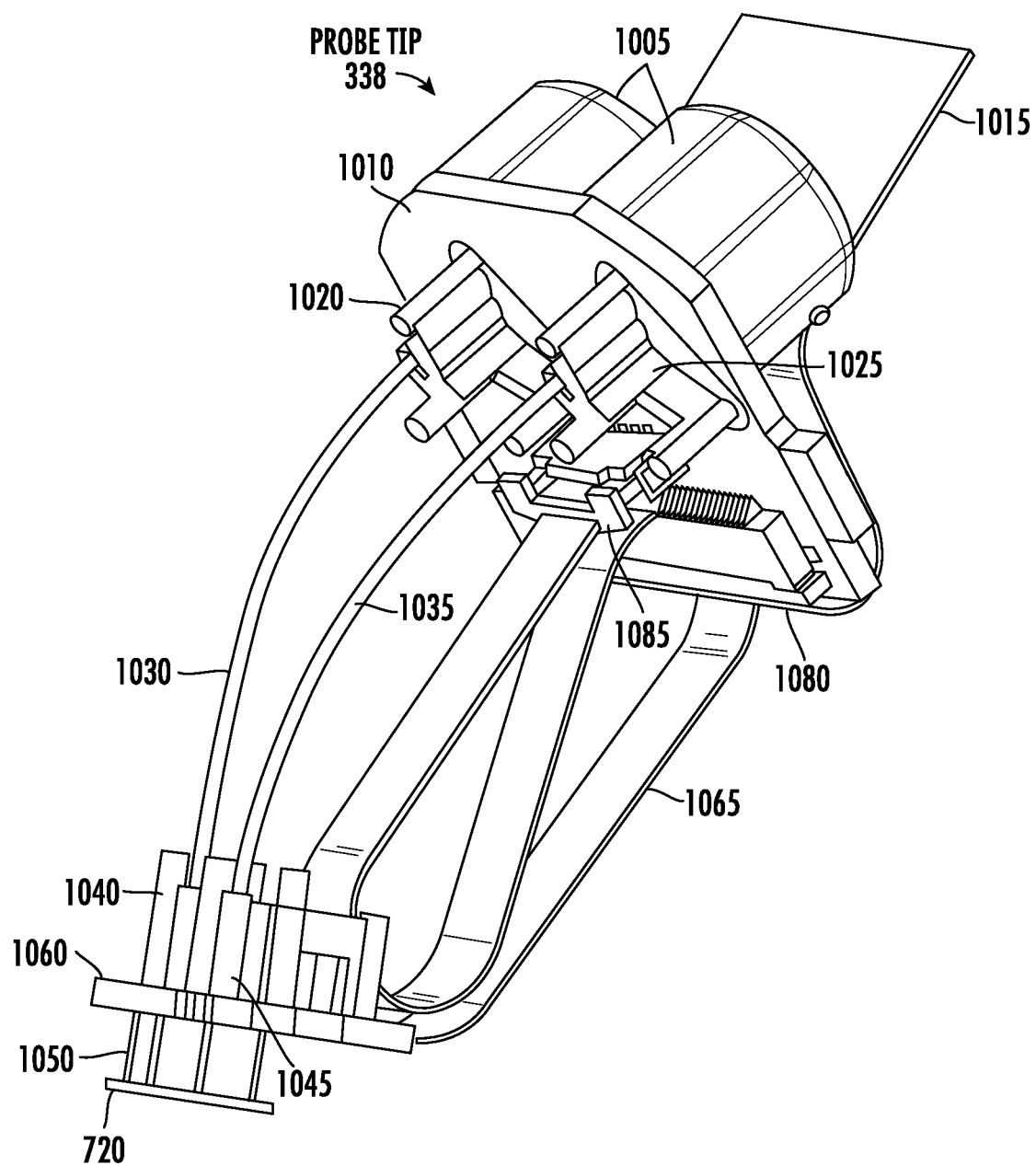
FIG. 12 shows the probe tip separate from the housing of the system unit and shows additional elements of the probe tip.

FIG. 12 shows the probe tip separate from the housing of the system unit and shows additional elements of the probe tip. As shown in this figure, the probe tip additionally includes an aperture plate 720, a first electrical connector 1080, and a second electrical connector 1085.

Figure 13:
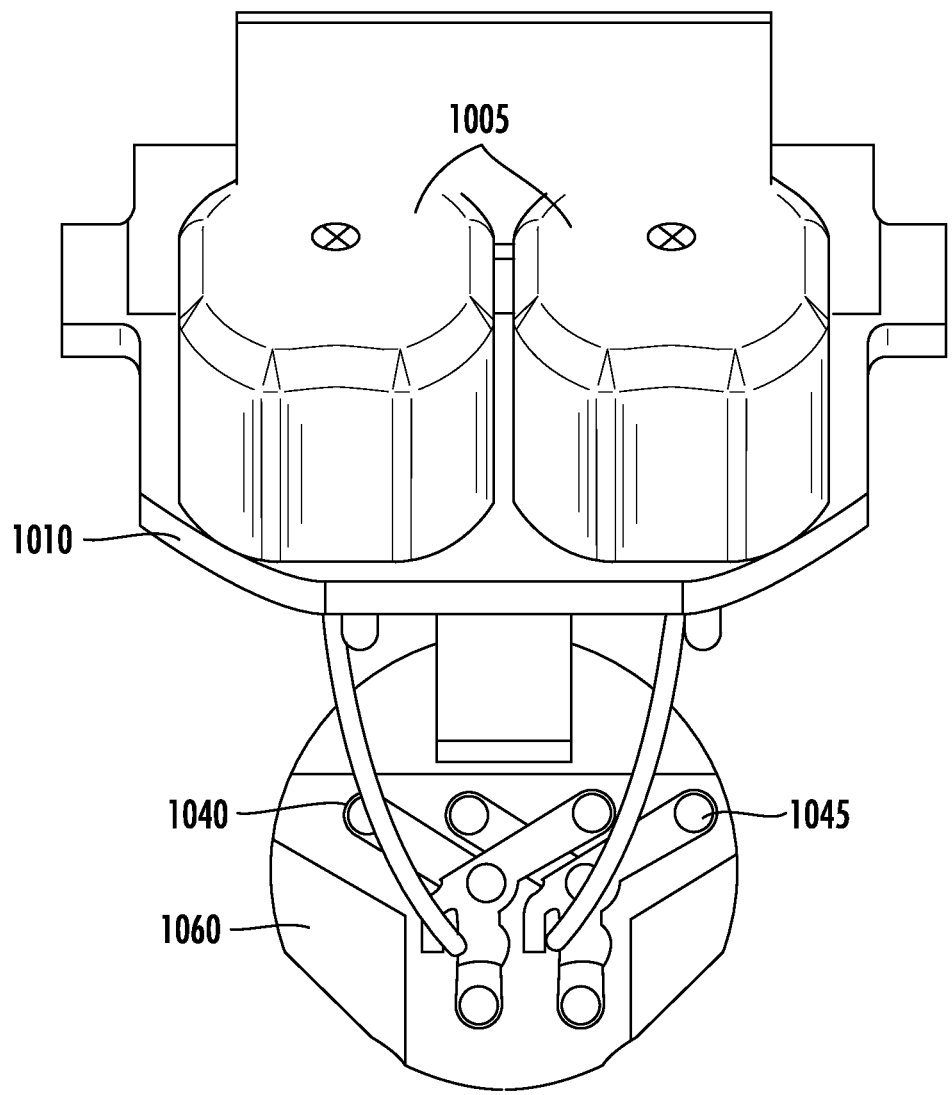
FIG. 13 shows a back view of the probe tip.

FIG. 13 shows a back view of the probe tip. This figure shows the two reflector domes 1005 mounted on the LED PCB 1010. Each reflector dome can direct light received from one or more LEDs into one of the optical fibers.

Figure 14:
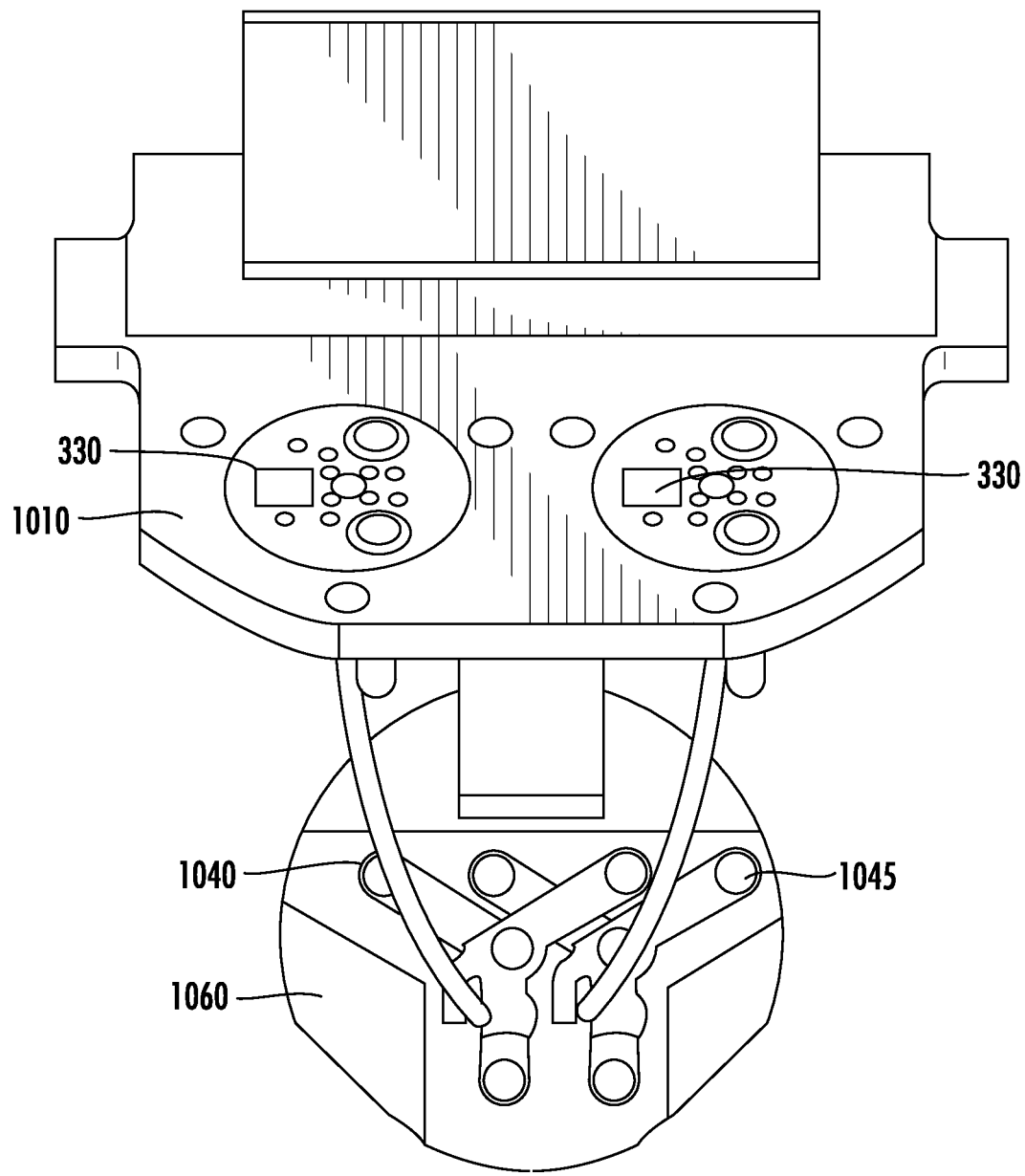
FIG. 14 shows a top view of the LED PCB with the reflector domes removed from the LED PCB.

FIG. 14 shows a top view of the LED PCB 1010 with the reflector domes removed from the LED PCB. One or more LEDs (e.g., four LEDs) can be mounted on the LED PCB under each reflector dome. The LED PCB can include one or more apertures, which portions of the optical fibers holder can extend into for adhesion of the optical fiber holder to the LED PBC.

The LED PCB can include one or more temperature sensors 330 (e.g., two temperature sensors). The temperature sensors can be mounted on the same side of the LED PCB that the LEDs and reflector domes are mounted on or can be mounted on the opposite side of the LED PCB that the LEDs and reflector domes are mounted on. The temperature sensors can be mounted respectively under the reflector domes when the reflector domes are mounted on the LED PCB. Each temperature sensor can independently transmit temperature information to the processor via one or more A-to-D converters (not shown). The temperature sensors can be thermistors, resistance temperature detectors (RTDs), thermocouples, semiconductor-based sensors (e.g., silicon diodes), infrared light detectors, or other types of temperature sensors.

Figure 15:
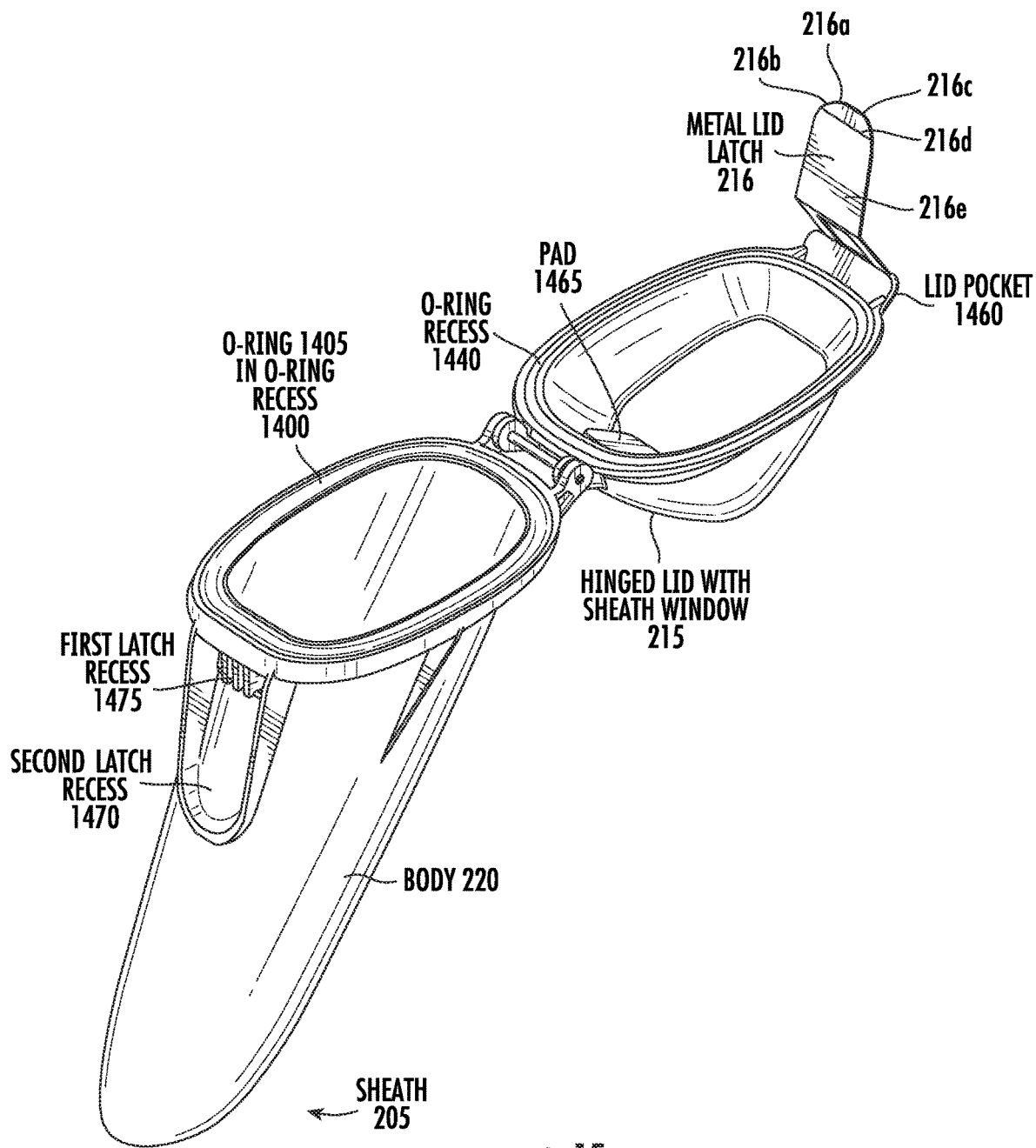
FIG. 15 shows a perspective view of the sheath, in an implementation.

FIG. 15 shows a perspective view of the sheath 205, in an implementation. The lid 215 is shown in an open position with respect to the body 220 where a system unit can be inserted into the sheath or removed from the sheath. The hinge that connects the lid and the body can be on a backside of the sheath. The body can include an o-ring recess 1400 of the top of the body. An o-ring 1405 is shown in the recess. The lid can also include an o-ring recess 4110 on the bottom of the lid. The o-ring recesses of the body and lid can contact the o-ring when the lid is closed against the body. The o-ring can form a seal that seals the lib to the body so that contaminants cannot enter the seal between the lid and body.

The latch can have a rounded end 216a and rounded corners 216b at the end of the latch. The end, corners, and edges of the latch can be relatively smooth. The smooth surface will not tear surgical gloves when the sheath and system unit are used.

Figure 16:
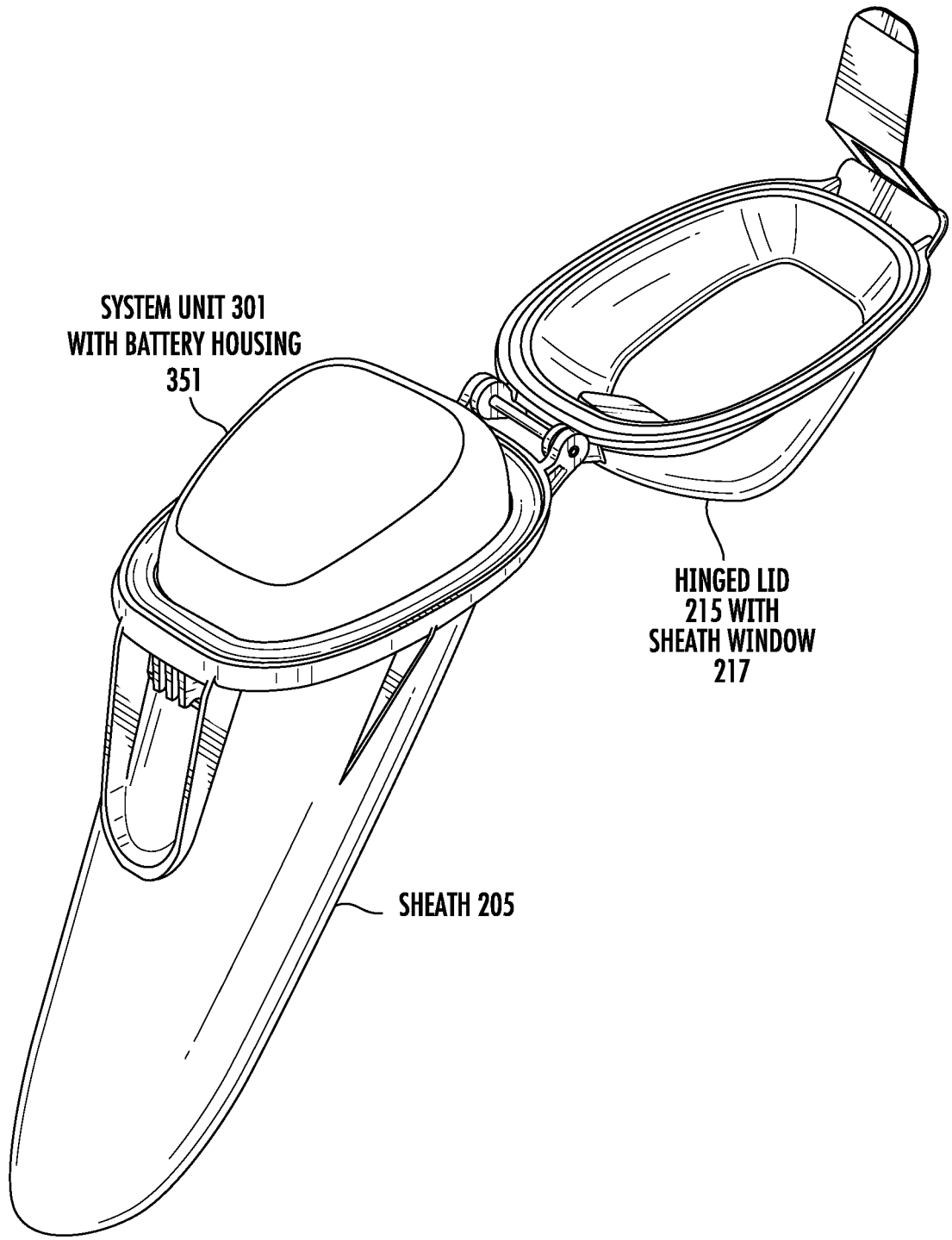
FIG. 16 shows a perspective view of the sheath, system unit, and power block, in an implementation.

FIG. 16 shows a perspective view of the sheath, system unit, and power block, in an implementation. The sheath is shown with the sheath lid open and the system unit with the power block attached is in the sheath. The probe face of the system unit may be in contact with the second window of the sheath.

Figure 17:
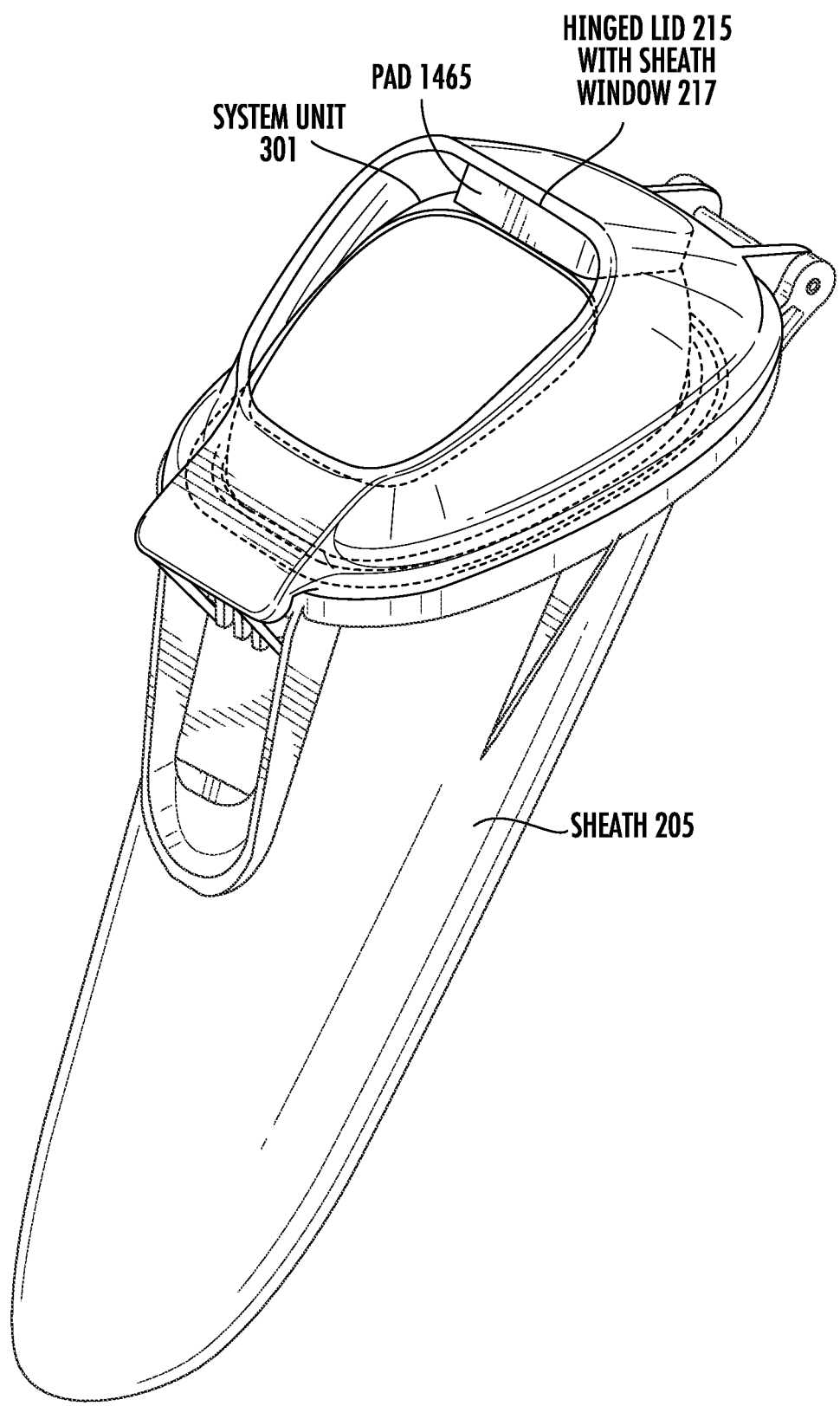
FIG. 17 shows a perspective view of the sheath, system unit, and power block, in an implementation.

FIG. 17 shows a perspective view of the sheath, system unit, and power block, in an implementation. The sheath is shown in FIG. 17 with the lid 215 closed against the body 220 of the sheath and with the latch in a latched position against the body. The lid may be formed of a first plastic material that can be transparent (e.g., the window of the lid), translucent (e.g., portions of the lid attached to the window), opaque, or any combination of these properties. The body may be formed of a second plastic that can be transparent, translucent, opaque, or any combination of these properties. The second window of the body may be attached to the body via an adhesive (e.g., epoxy), plastic weld, or other fasteners. The second widow may form a seal with the body where the second window attaches to the body where contaminants cannot pass through the seal to contaminate a system unit in the sheath via the seal.

The display of the system unit is visible through the first window of the lid of the sheath. Information (e.g., text, graphics, or both) that is displayed on the display of the system unit is visible to a user looking through the second window of the lid. The display and window are both proximally located with the probe face and second window distally located when the system is ready for use. With the second window in contact with tissue, the display faces away from the tissue so that the display, through the first window, can be seen by a user.

Figure 18:
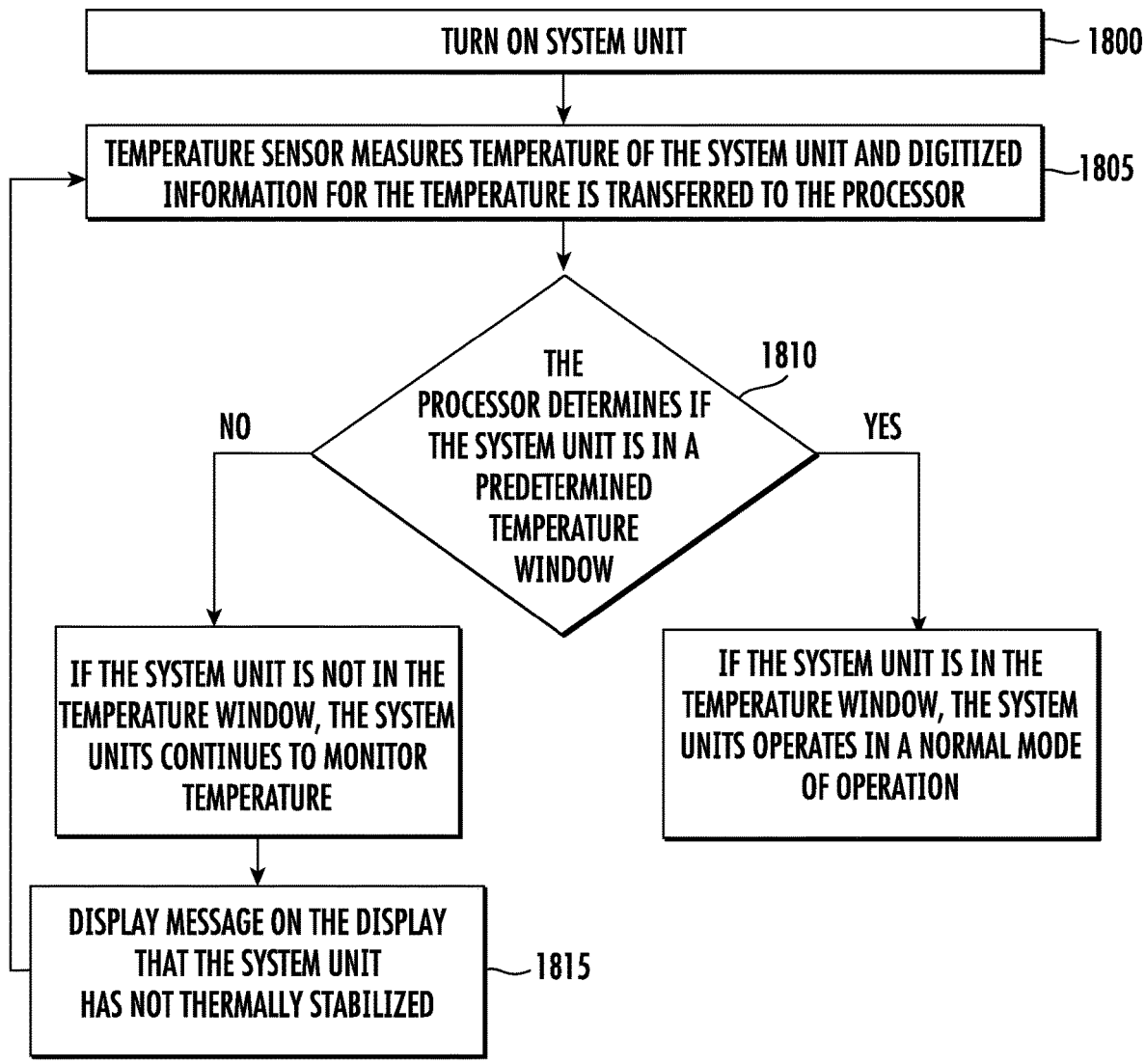
FIG. 18 is a flow diagram of a method of determining whether the system unit or a portion of the system unit is at a temperature in a predetermined temperature range for making oximetry measurements, in an implementation.

FIG. 18 is a flow diagram of a method of determining whether the system unit or a portion of the system unit, such as inside one or both of the reflector domes, is at a temperature in a predetermined temperature range for making oximetry measurements, in an implementation. The flow diagram shows an example embodiment in an implementation. Steps may be added, removed, or combined without deviating from the method.

At 1800, the system unit is turned on. The system unit may be in the sheath.

At 1805, one or more temperature sensors measure the temperature of the system unit and digitized information for the temperature is transferred to the processor. The temperature of the system unit can be measured under the reflector domes or at other locations inside or outside the system unit.

At 1810, the processor determines if the system unit is at a temperature that is in a predetermined temperature range. The processor may average the temperature information received from the temperature sensors or may determine if the system unit is in the predetermined temperature range by determining if a temperature sensor reporting a highest temperature is above the predetermined temperature range or determining if a temperature sensor reporting a lowest temperature is below the predetermined temperature range.

In an embodiment, the predetermined range of temperatures is about 40.5 degrees Celsius to about 41.5 degrees Celsius. In an embodiment, the predetermined range of temperatures is about 40.9 degrees Celsius to about 41.1 degrees Celsius (e.g., 41 degrees Celsius+ or − about 0.1 degrees Celsius). The temperature sensor may be able to measure a temperature range of about 20 degrees Celsius to about 50 degrees Celsius. If the processor determines that the system unit is not in the predetermined temperature range, the system unit may not take oximetry measurements. And may continue to monitor the temperature of the unit.

At 1815, the system unit may display a message on the display indicating that the system unit needs thermally stabilize (i.e., warm up or cool down) for normal operations (e.g., to take oximetry measurements). The system unit may display a message on the display indicating steps that can be taken for warming up the system unit to thermally stabilize for normal operations (e.g., to take oximetry measurements). The displayed message may indicate that the system unit can be placed on a heating pad, hold the system unit in an operator's hand, or other steps, to heat the system unit. The system unit may also power on the LEDs to warm up the system unit. The LEDs may be sequentially powered on and off (e.g., LEDs 1 through 8 powered on and then off sequentially). When each LED is powered on, the power provided to the LED may be modulated power that is modulated by a sine wave or other power function to warm up the LED and the system unit. The LEDs may be sequentially powered on by DC power where a high DC power level is the highest power level supplied by the modulated power (e.g., peak power supplied by the sine wave modulated power). Power supplied to the LEDs for warming up the system unit is described further below.

The system unit may alternatively display a message on the display indicating that the system unit needs to cool down to thermally stabilize for normal operations (e.g., to take oximetry measurements). The system unit may display a message on the display indicating steps that can be taken for cooling the system unit, such as a message instructing an operator to remove the system unit from an operator's hand, placing the system unit on a table, or other steps. The system unit may also continue to provide power to the LEDs to cool down the system unit. The LEDs may be sequentially powered on and powered off. The power supplied to each LED when powered on may be modulated, such as by a waveform having a relatively low duty cycle (e.g., less than 50 percent on time per cycle). Powering the LEDs with a relatively low duty cycle wave allows the system unit to cool, but cool at a low rate so that the temperature of the system unit does not undershoot the low-temperature limit (e.g., 40.9 degrees Celsius) or does not undershoot the low-temperature margin by a large amount (e.g., 2 degrees Celsius). The LEDs may also be turned off to cool the system unit. Power supplied to the LEDs for cooling down the system unit is described further below.

In an implementation where the system unit is at or above a safety high-temperature point (e.g., 45 degrees Celsius or above), the system unit will shut down one or more elements. The elements that may be such down can include the LEDs. The message for cooling the system unit when the system unit is at or above the safety high point may be more prominent than the message to cool when the system unit is not at or above the safety high point. For example, the message to cool the system unit might flash, be in a prominent color (e.g., red, bright green, or another color), may be displayed with an alert noise, may be displayed with a vibration of the system unit, or other display technique.

If the processor determines that the system unit is in the predetermined temperature range, the system unit may operate for taking oximetry measurements. If the system unit is in the predetermined temperature range, the system unit will operate according to predefined parameters and any calibration information stored in the system unit for the operation of the light sources (e.g., LEDs), photodetectors, or both will be valid.

Figure 19:
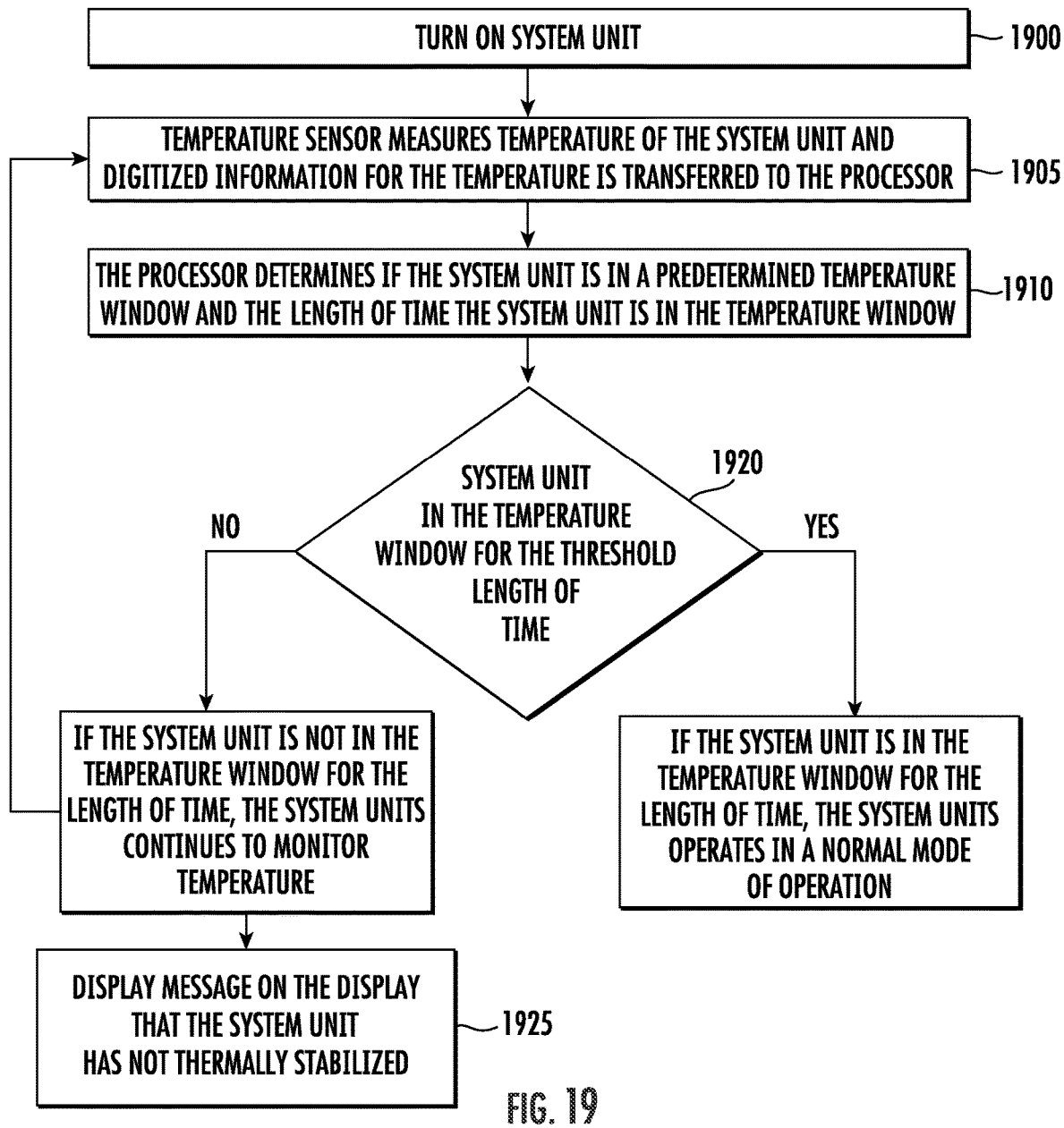
FIG. 19 is a flow diagram of a method of determining whether the system unit or a portion of the system unit is at a temperature in a predetermined temperature range for making oximetry measurements, in an implementation.

FIG. 19 is a flow diagram of a method of determining whether the system unit or a portion of the system unit, such as inside one or both of the reflector domes, is at a temperature in a predetermined temperature range for making oximetry measurements, in an implementation. The flow diagram shows an example embodiment in an implementation. Steps may be added, removed, or combined without deviating from the method.

At 1900, the system unit is turned on. The system unit may be in the sheath.

At 1905, one or more temperature sensors measure the temperature of the system unit and digitized information for the temperature is transferred to the processor. The temperature of the system unit can be measured under the reflector domes or at other locations inside or outside the system unit.

At 1910, the processor determines if the system unit is at a temperature that is in a predetermined temperature range. The processor may average the temperature information received for the temperature sensors or may determine if the system unit is in the predetermined temperature range by determining if a temperature sensor reporting a highest temperature is above the predetermined temperature range or determining if a temperature sensor reporting a lowest temperature is below the predetermined temperature range.

At 1920, the processor determines whether the system unit has been in the predetermined temperature range for a predetermined amount of time. The predetermined time limit may be about 10 seconds to about 5 minutes. In a specific implementation, the predetermined time limit is about 20 seconds.

If the processor determines that the system unit has not been in the predetermined temperature range for a predetermined amount of time, the system unit may not take oximetry measurements. And may continue to monitor the temperature of the unit.

At 1925, the system unit may display a message on the display indicating that the system unit needs to thermally stabilize for normal operations (e.g., to take oximetry measurements).

The system unit may display a message on the display indicating steps that can be taken for warming up the system unit, such as displaying a message to place the system unit on a heating pad, hold the system unit in an operator's hand, or other steps.

The system unit may also supply power to the LEDs to warm up the system unit. The LEDs may be sequentially powered on and off (e.g., LEDs 1 through 8 powered on and then off sequentially). When each LED is powered on, the power provided to the LED may be modulated power that is modulated by a sine wave or other power function to warm up the LED and the system unit. The LEDs may be sequentially powered on by DC power where a high DC power level is the highest power level supplied by the modulated power (e.g., peak power supplied by the sine wave modulated power). Power supplied to the LEDs for warming up the system unit is described further below.

The system unit may alternatively display a message on the display indicating that the system unit needs to cool down (e.g., thermally stabilize) for normal operations (e.g., to take oximetry measurements). The system unit may display a message on the display indicating steps that can be taken for cooling the system unit, such as a message instructing an operator to remove the system unit from an operator's hand, placing the system unit on a table, or other steps.

The system unit may also continue to provide power to the LEDs to cool down the system unit. The LEDs may be sequentially powered on and powered off. The power supplied to each LED when powered on may be modulated, such as by a waveform having a relatively low duty cycle (e.g., less than 50 percent on time per cycle). Powering the LEDs with a relatively low duty cycle wave allows the system unit to cool, but cool at a low rate so that the temperature of the system unit does not undershoot the low-temperature limit (e.g., 40.9 degrees Celsius) or does not undershoot the low-temperature margin by a large amount (e.g., 2 degrees Celsius). The LEDs may also be turned off to cool the system unit. Power supplied to the LEDs for cooling down the system unit is described further below.

In an implementation where the system unit is at or above a safety high-temperature point (e.g., 45 degrees Celsius or above), the system unit will such down one or more elements. The elements that may be such down can include the LEDs. The message for cooling the system unit when the system unit is at or above the safety high point may be more prominent than the message to cool when the system unit is not at or above the safety high point. For example, the message to cool the system unit might flash, be in a prominent color (e.g., red, bright green, or another color), may be displayed with an alert noise, may be displayed with a vibration of the system unit, or other display technique.

In another implementation, if the system unit is at or above a safety high-temperature point, the duty cycle of the power supplied to the LEDs may be adjusted to lower the amount of time that the LEDs are on. Thereby, the system unit may cool at a relatively low rate and not undershoot the lower temperature of the operating temperature range.

In an implementation, if the processor determines that the system unit has been in the predetermined temperature range for a predetermined amount of time, the system unit may operate for taking oximetry measurements. If the system unit is in the predetermined temperature range, the system unit will operate according to predefined parameters and any calibration information stored in the system unit for the operation of the light sources (e.g., LEDs), photodetectors, or both will be valid.

In an implementation, if the system unit has previously taken oximetry measurements and the temperature of the system unit goes out of the predetermined temperature range, the system unit will not display any previously determined oximetry measurements. Additionally, the messages for warming or cooling the system unit may be displayed on the display if the temperature of the system unit is below or above the predetermined temperature range.

In an implementation, the system unit will enter a standby mode if the system unit does not take an oximetry measurement for a predetermined length of time. The predetermined length of time may be about 30 seconds or longer. In a specific implementation, the predetermined length of time is about 2 minutes. The system unit can conserve the energy stored in the power pack by entering the standby mode. In the standby mode, the LEDs may be off, or the duty cycle of the power signal supplied to the LEDs may be adjusted to lower the amount of time that the LEDs are on. Other elements of the system unit may be left on to keep the system unit in the predetermined temperature window for normal operations for taking oximetry measurements. For example, the circuits on the processor PCB may stay powered on, the display may be powered on, the detectors may be powered on, or any combination of these elements may be powered on while the others of the elements are powered down. In the standby mode, the accelerometer may stay powered on. The processor may place the system unit in a power-up mode when the accelerometer detects a movement of the system unit, such as an operator picking up the unit. In an embodiment, actions, such as placing the system unit in a power-up mode, that are described as being carried out by the processor, may be carried out by a field programmable gate array (FPGA) that is included in the system unit and connected to the system bus 303. In an embodiment, the system unit does not include a processor and includes an FPGA that manages the processing for the system unit. In an embodiment, the system unit's processor and FPGA manage the processing for the system unit.

Figure 20:
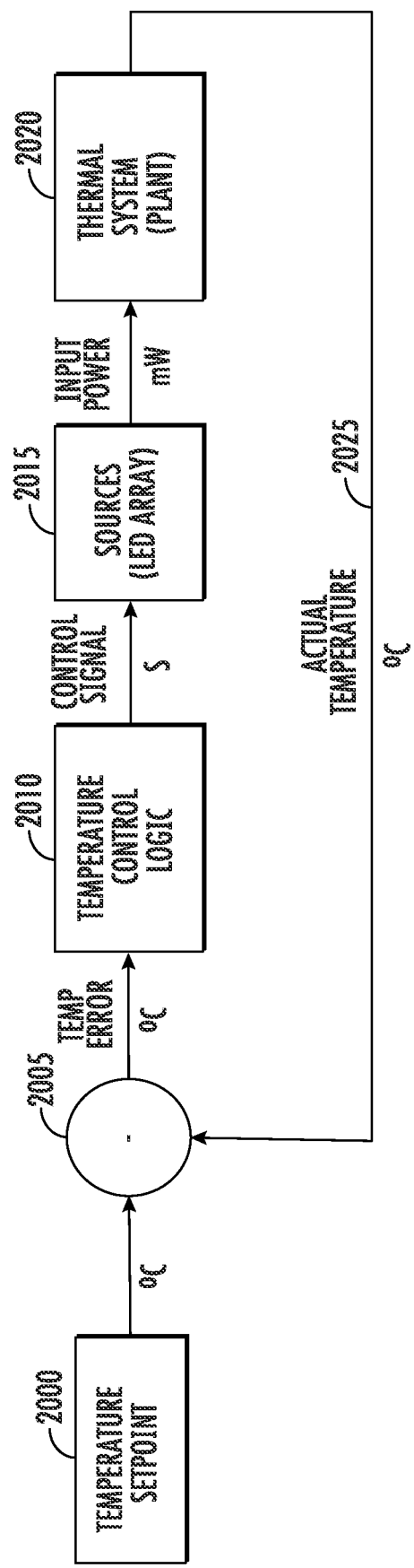
FIG. 20 is a block diagram showing a temperature control system of the system unit.

FIG. 20 is a block diagram showing a temperature control system of the system unit. The temperature control unit facilitates power control of the power supplied to the LEDs of the system unit for controlling the temperature of the system unit. The temperature control system may include digital control circuits, analog control circuits, a combination of digital and analog control circuits, firmware, software, or a combination of these elements.

In an implementation, the temperature control system includes a temperature control input port 2000, an adder circuit 2005, a temperature control logic circuit 2010, the light sources 2015 (e.g., the LEDs of the signal emitter 332), a thermal system 2020, and a feedback link 2025. While a number of the elements of the system unit described are described as a circuit, in some implementations, one or more of the elements are computer code elements operable on various circuits of the system unit, such as the system unit's processor. The computer code can be stored in one or more of the memories of the system unit.

In an implementation, temperature control input port 200 is adapted to receive first temperature information for the temperature setpoint of the system unit from the system unit's processor and provide the temperature information to the adder circuit. The temperature setpoint may be 41 degrees Celsius + or − from about 0.1 degrees Celsius to about 0.5 degrees Celsius.

The temperature control input port is a first input port for adder circuit 2005, which receives the first temperature information provided by the processor. Adder circuit is connected to feedback link 2025, which is a second input port for adder circuit 2005. The feedback link is adapted to provide second temperature information to the adder circuit. The second temperature information may be temperature information for the actual temperature of the system unit. More specifically, the second temperature information may be temperature information for the temperature inside reflector domes 1005 where the temperature sensors are located (FIGS. 13-14).

Adder circuit 2005 is adapted to determine a difference between the first and second temperature information and transmit the temperature difference information to temperature control logic circuit 2010. The temperature control logic circuit is adapted to generate a power control signal for modulating the power that powers LEDs 2015 based on the temperature difference information. The power supplied to the LEDs drives the temperature of the system unit towards the temperature setpoint.

Thermal system 2020 is adapted to receive the temperature signal generated by the temperature sensors, which are located adjacent to the LEDs inside the reflector domes. The thermal system is configured to generate the second temperature signal that is transmitted to the adder circuit through feedback link 2025. In an implementation, DAC 332 is a circuit located between the processor and the adder circuit. In an implementation, the DAC is a circuit in the temperature control logic circuit. In an implementation, the DAC is a circuit located in the LED array.

As described briefly above with respect to FIG. 18 at 1815, FIG. 19 at 1925, and FIG. 20, temperature control logic circuit 2010 is adapted to control the power supplied to the of the LEDs (four LEDs located under each reflector dome on LED PCB 1010) by modulating the average drive currents of the eight LEDs.

When the system unit is operating in a normal data-collection mode for generating oximetry data (e.g., making oximetry measurements and generating oxygen saturation information), the power (i.e., drive current) provided to each of the LEDs is sinusoidally modulated for a fixed period of time. Thus, the light generated by each of the LEDs is sinusoidally modulated for the fixed period of time. After the LEDs have been power modulated sequentially for identical periods of time, the temperature of the system unit is measured by the temperature sensors for the period of time that one of LEDs is powered on for.

The power supplied to the LEDs causes the LEDs to operate at a temperature above the ambient temperature inside the system unit. Thus, the LEDs can cause the temperature of the system unit to increase. While the LEDs are described above as operating above the ambient temperature of the system unit, in some environments the LEDs operate at a temperature below the ambient temperature of the system unit.

If the system unit is above the temperature setpoint (e.g., 41 degrees Celsius + or −0.5 degrees Celsius) after power is provided to the LEDs, the system unit may be cooled after the heating period. In an implementation, cooling of the LEDs and system unit is facilitated by not supplying power to the LEDs for the period of time that a single LED is powered on. Alternatively, the duty cycle of power supplied to the LEDs may be adjusted to that power is provided to the LEDs for less than half of the period of a power cycle (e.g., less than half of a sinusoid period of power provided). Altering the duty cycle allows the LEDs to provide heat at a rate where the system unit can cooled, but not undershoot the temperature setpoint or undershoot the temperature setpoint by a relatively small amount.

In an embodiment, if the temperature of the system unit is below the temperature setpoint (e.g., 41 degrees Celsius + or − about 0.1 degrees Celsius), the LEDs are powered on to facilitate the heating. Additional heating by the LEDs is facilitated achieved by supplying Peak power (e.g., the power provided at the highest power provided from the sinusoidal power) can be supplied to the LEDs for the period of time that one or more of the LEDs are driven sequentially for an oximetry measurement cycle.

Heating or cooling is periodically stopped so that oximetry information may be generated and displayed on the display of the system unit. The heating or cooling and oximetry measurements may be made at a cycling rate of approximately 0.5 Hz or higher.

Figure 21:
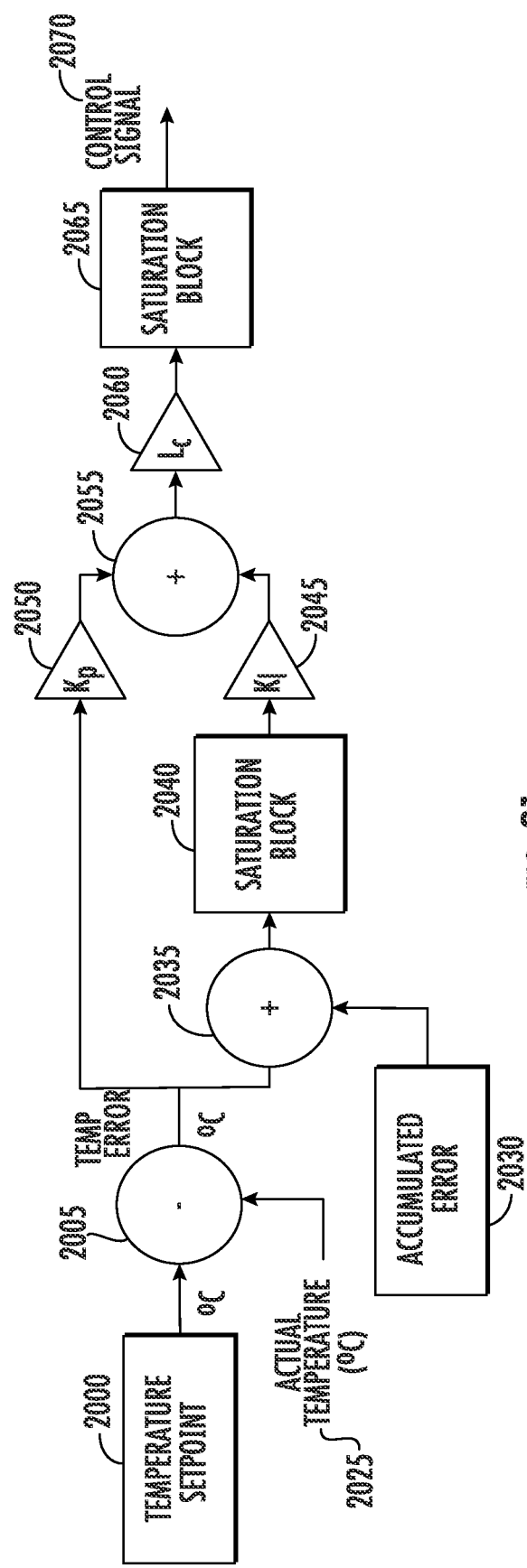
FIG. 21 is a block diagram of a temperature control logic circuit, in an implementation.

FIG. 21 is a block diagram of temperature control logic circuit 2010, in an implementation. The temperature control logic circuit is adapted to implement the heating and cooling of the system unit described above. In an implementation, the temperature control logic circuit is a proportional-integral (PI) controller. In an implementation, the PI controller does not have a derivative controller. The temperature controller in an alternative implementation is a proportional-integral-derivative (PID) controller. The temperature controller in an alternative implementation is a proportional P controller. The temperature controller in an alternative implementation is an integral (I) controller. The temperature controller in an alternative implementation is an integral-derivative (ID) controller. While the temperature control logic circuit is described as a circuit, the functionality described below that that the circuit implements may alternatively be implemented in computer code that operable on the processor, another circuit included in the system unit, or both.

In an implementation, the temperature control logic circuit 2010 implements a PI control loop that generates one or more control signals based on the sign and magnitude of the temperature error and an integrated temperature error. The temperature error signal for the temperature error is the difference between the setpoint temperature and the actual temperature of the system unit determined by adder circuit 2005.

The PI control loop includes the temperature setpoint port 2000, adder circuit 2005, feedback link 2025, an error accumulator 2030, a saturation block 2040, first gain circuit 2045, a second gain circuit 2050, an adder circuit 2055, a gain adjustment circuit 2060, a saturation block 2065, and the control signal port 2070 that provides the control signal to the LEDs.

In an implementation, the output port of adder 2005 is connected to the input ports of both the adder 2035 and the first gain circuit. The accumulated error circuit 2030 includes an output port that is connected to an input port of adder circuit 2035. An output port of adder circuit 2035 is connected to an input port of saturation block 2040, and an output port of the saturation block is connected to an input port of the second gain circuit 2045. The output ports of the first and second gain circuit are connected to the input ports of adder 2055, and an output port of adder 2055 is connected to the gain adjustment circuit 2060. An output port of the gain adjustment circuit is connected to an input port of saturation block 2065, and an output port of the saturation block is adapted to provide the control signal to the LEDs.

A first gain path includes the first gain circuit and a second gain path includes adder 2035, saturation block 204, and second gain circuit 2045 are arranged as parallel paths. The first gain path is the proportional gain path adapted to provide proportional gain based on the temperature error signal. The second gain path is the integral gain path adapted to provide integral gain based on the temperature error signal. In an implementation, the control loop circuit includes a third gain path that is in parallel with the first and second gain paths and is a derivative gain path that provides derivative gain based on the temperature error signal.

The proportion gain generates a gain proportional to the error signal. The proportional gain may have a tendency to oscillate. The integrated gain path has a tendency to damp the oscillation and allow the control signal to control the LEDs so that the LEDs can place and hold the system unit at the temperature setpoint.

In addition to PI control, the temperature controller is adapted to perform two additional features, which improve the performance of the system unit. The PI controller May 1) perform integral windup mitigation and 2) may correct for asymmetrical cooling and heating. Integral windup, also known as integrator windup or reset windup, refers to a situation in the PI controller where a large change in the temperature setpoint occurs (such as when the system unit is first powered on for use) and the integral term accumulates a significant error during the temperature rise, thus allowing the temperature to overshoot and continue to increase as the accumulated error is unwound.

Integral windup is mitigated by the PI controller by accumulating an integrated temperature error up to a predetermined high value, which may be stored in the system unit. The PI controller may not accumulate integral windup more than the predetermined high value. Thus, relatively large integrated error buildup may be prevented, particularly during system unit warm up when the temperature error in the system is present for a relatively long time duration.

Asymmetry of heating and cooling conditions is corrected by a gain adjustment factor. The system unit has active heating capability by use of the LEDs, but cools passively through heat dissipation. The active heating and passive cooling results in a smaller time constant for increasing the temperature of the system unit than for reducing the temperature of the system unit.

The performance of the PI control loop is driven by the 6 configurable parameters shown in Table A below. The parameters may be set by the circuits, may be stored in memory and used with the circuits or used in a software implantation of the PI control loop, or a combination of these implementations. The parameters in Table A are for one implementation. The parameters may be different for different implementations. For example, the temperature setpoint may be 37.5 degrees Celsius + or − about 0.1 degrees Celsius. The proportional gain may range from 1.2 to 1.7. The integral gain may range from 0.04 to 0.075. The gain adjustment may range from 1.1 to 1.3.

TABLE A

| Parameter | Parameter Name | Sample Value | Description |
| --- | --- | --- | --- |
| Temperature Setpoint | $T_{set}$ | 49.5-41.5 [° C.] | Actual thermistor temperature is compared to this value to produce an error signal. |
| Proportional Gain | $K_P$ | 1.5 [s/° C.] | Temperature error is multiplied by this gain to produce the proportional control signal. |
| Integral Gain | $K_I$ | 0.0625 [s/(cycle*° C.)] | Integrated temperature error is multiplied by this gain to produce the integral control signal. |
| Gain Adjustment Factor (for negative error) | $L_C$ | 1.2 [none] | This adjustment factor accounts for the asymmetry of the actuation signal (power input). The system has active heating available to quickly raise the temperature, but no active cooling to lower temperature. |
| Integrator Saturation | $I_{MAX}$ | 15 [cycle*° C.] | Integrated error may never be larger than this magnitude. This prevents integral windup during warm up. |
| Maximum Length, Temp Control Period | $t_{max}$ | 1.67 [s] | Maximum length of temperature control period. Increasing this value will increase the maximum effective input power and decrease the minimum effective input power of the device. |

The logic of the control loop is described below with respect to the parameters in the table. The actual temperature is compared to the setpoint temperature to produce the temperature error by adder circuit 2005.

Two things are done with this temperature error value. In the proportional gain path (upper path), the temperature error is multiplied by the proportional gain Kp, by proportional gain circuit 2050 and the result (i.e., the proportional control signal of the PI control loop) of the gain is transferred to adder circuit 2005.

In the integral path (lower path), the temperature error is added to the accumulated error that is accumulated by the integral error accumulator 2030 by adder circuit 2035. Thereafter, the accumulated error is saturated to a maximum magnitude (e.g., a maximum magnitude) of IMAX by saturation block 2040. The resulting value generated by the saturation block is the total integrated error generated by the integral path, and is multiplied by the integral gain KI by the integral gain circuit 2045, and the result (i.e., the integral control signal of the PI control loop) is transmitted to adder circuit 2055.

The sum of the proportional control signal and the integral control signal generated by adder circuit 2055 is multiplied by the gain adjustment factor Lc by gain adjustment circuit 2060, if the instantaneous temperature error is negative.

Thereafter, the control signal is saturated by saturation block 2065 in order to limit the length of the following temperature control period. The resulting control signal determines the value of the time on and the time off of the LEDs in a heating cycle following a current heating cycle.

Determining readiness to display oxygen saturation measurements. For every oxygen saturation information measurement made during a data acquisition cycle, the temperature control logic (e.g., the circuits or the firmware of the system unit) takes a temperature measurement, determines the temperature of the system unit, and adjusts the effective heating rate performed by the LEDs according to the logic described above. The temperature control logic also transfers the determined temperature information to the system unit's processor, which determines whether to display the oxygen saturation information.

In addition to modifying the logic used to control the device temperature, the way in which the system unit uses the temperature information to display or disqualify an oxygen saturation measurement has also been modified. The system unit will display the oxygen saturation information on the display when the recent temperatures of the system unit fall inside a +/−0.1° C. tolerance envelope.

In addition, the system unit may not display the oxygen saturation information until the system unit has successfully completed warm up and the temperature is substantially stable at the setpoint temperature. The system unit will reject brief noisy temperature data, which can occur during normal operation, and continue to display the oxygen saturation information.

Figure 22:
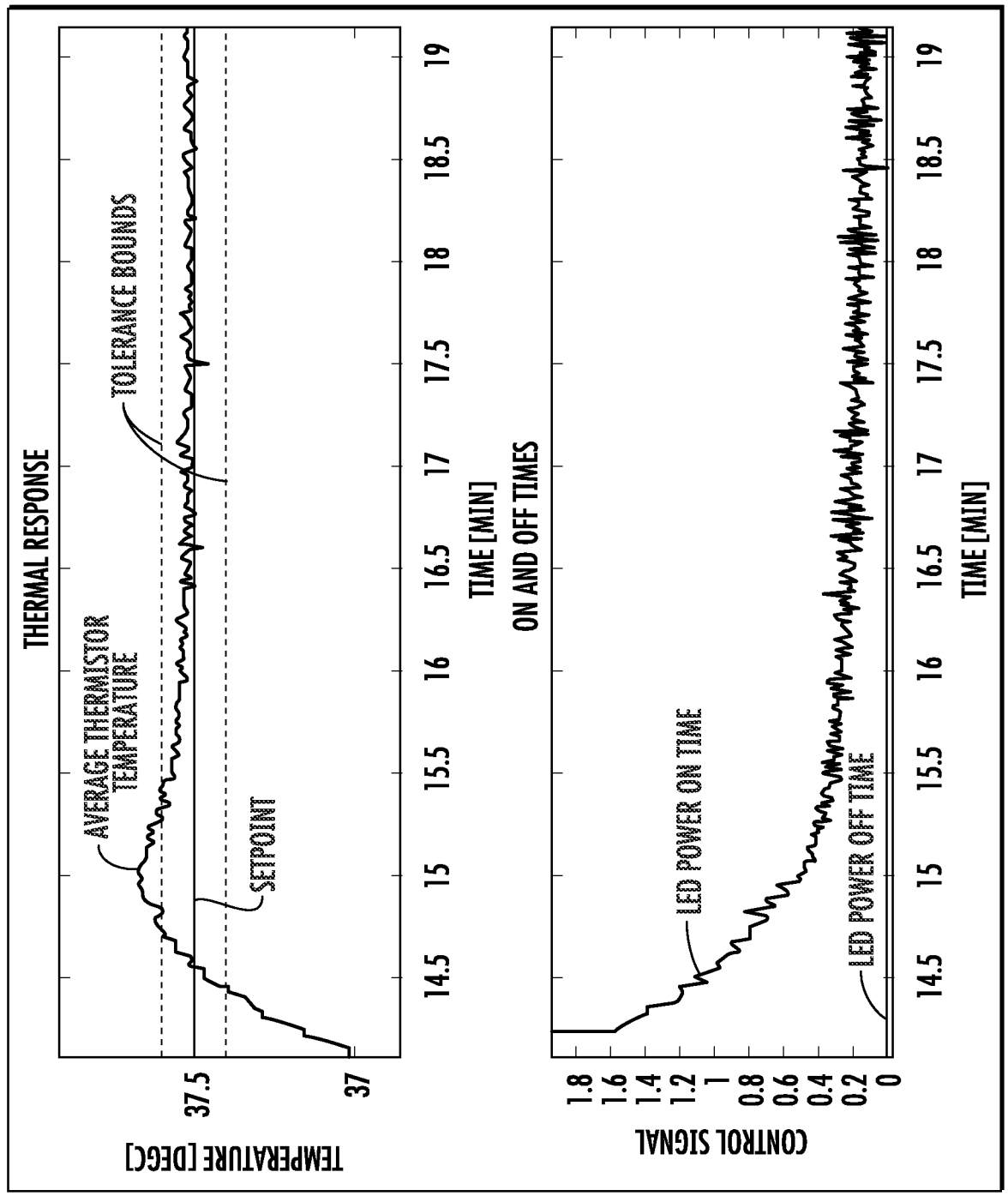
FIG. 22 shows an example of temperature overshoot and temperature pass through, in an implementation.

Determining when the system unit has achieved warm up and is thermally stable. During the warm up of the system unit, temperature overshoot can occur. That is, the temperature of the system unit rises above the setpoint temperature. Temperature overshoot can be caused by integral windup. Integral windup of the system unit during warm up from a power-on state has the following characteristics, in an implementation. The overshoot peak magnitude can be +0.20° C. above the temperature setpoint (i.e., +0.1° C. above the upper-tolerance bound of the temperature setpoint). The temperature of the system unit can be outside of upper-temperature bounds for about 30 seconds or more. The temperature of the system unit passes through the tolerance envelope for the temperature setpoint in about 20 seconds. FIG. 22 shows an example of the temperature overshoot and temperature pass through.

In an implementation, in order to prevent the system unit from briefly indicating that the temperature of the unit is within temperature bounds of the temperature setpoint during the unit's initial traverse through the tolerance envelope of the temperature setpoint, the temperature control logic circuit is started when the system unit is powered on.

After the system unit is warmed up and at the temperature setpoint, the system unit may change information that is displayed on the display. For example, the system unit may display a splash screen prior to temperature warm up and temperature stabilization and after temperature stabilization at the temperature setpoint, the system unit may display a display indicating that the system unit is ready to make oxygen saturation measurements and display measurement information for the measurements. Thereafter, the system unit may use a different set of rules for evaluating whether the system unit remains thermally stable within the temperature bounds of the temperature setpoint.

For example, after the system unit is powered on and is thermally within the temperature bounds of the temperature setpoint, but is not yet thermally stable (e.g., temperature may overshoot the temperature bounds of the temperature setpoint as described above after initial power up of the system unit), the system unit may determine whether the temperature of the unit is inside or outside of the tolerance bounds of the temperature setpoint. And, after each oximetry measurement cycle, the system unit may set a flag (e.g., a flag "in_tol" or in tolerance to either 0 or 1) to indicate whether the system unit is in tolerance or not in tolerance. Further, the system unit may maintain a running buffer of a number (e.g., 30) of the most recent values of the in_tol flag settings. During each oximetry measurement cycle, the oldest value in the in-tol flag stored in the buffer is discarded and a newest value of the in_tol flag is stored in the buffer (e.g., added to the top of the buffer). When a set number (e.g., 25) of the values in this buffer are, for example 1 (indicating an in-temperature tolerance oximetry measurement by the system unit), the system unit's warm up determination is completed.

Figure 23:
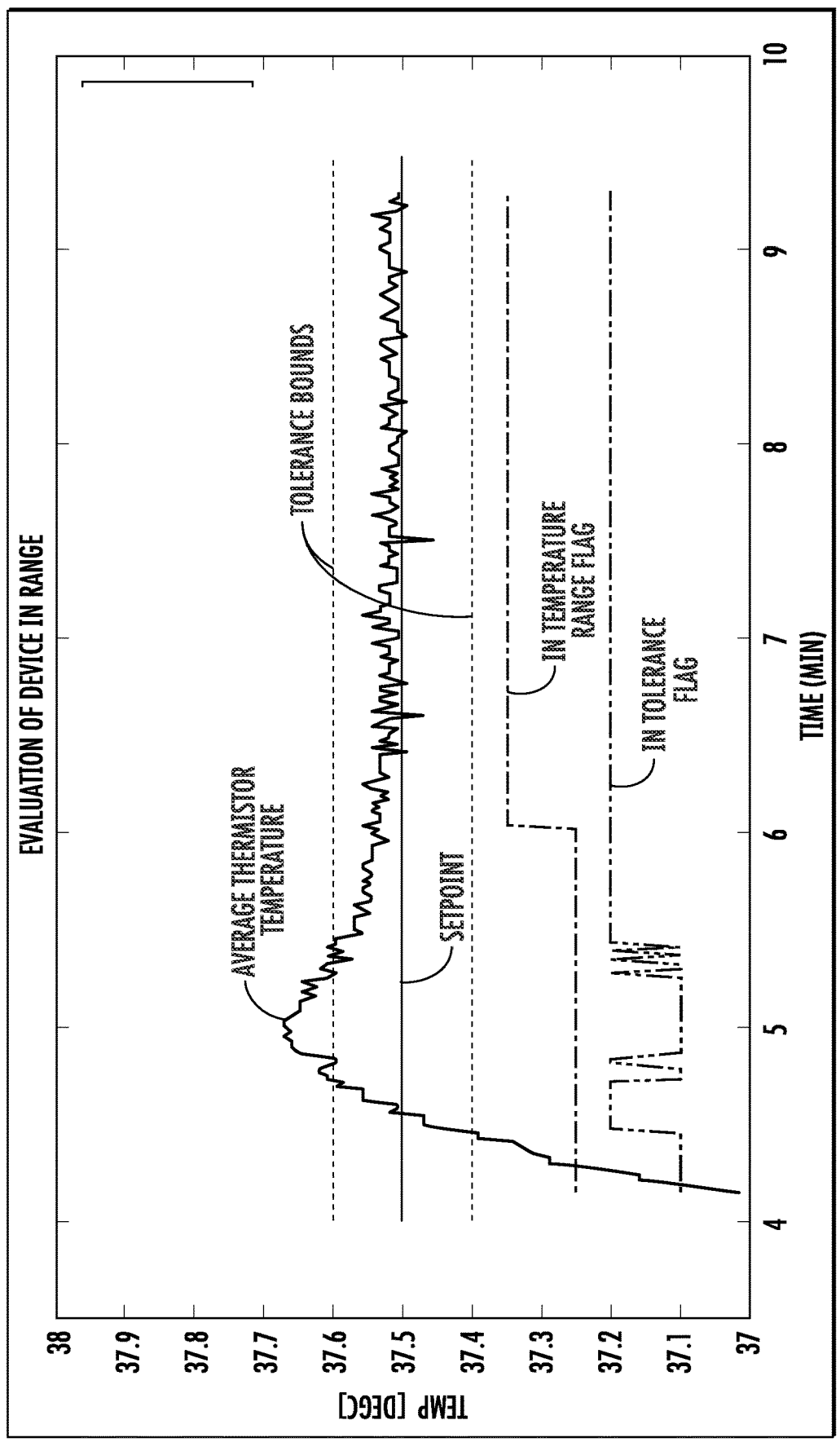
FIG. 23 shows the temperature of the system unit passing through and above the temperature bounds of the setpoint temperature during warm up.

This method inhibits the system unit from declaring that it is in range when it first passes through the temperature bounds of the setpoint temperature during warm up if fewer than 30 continuous cycles, for example, occur during warm up this stage. FIG. 23 shows the temperature of the system unit passing through and above the temperature bounds of the setpoint temperature during warm up. The figure also shows the intolerance temperature flag oscillating between 0 and 1, unit the system unit remains in the temperature bounds of the setpoint temperature. After the warm up is complete and the system unit remains in the temperature bound for 30 measurement cycles and warm up cycles, the system unit sets a flag that indicates that the warm up period has ended.

After the warm up of the system unit is completed and the system unit is thermally stable in the temperature bounds of the setpoint temperature, the splash screen displayed on the display is replaced by oximetry information (e.g., an oxygen saturation value of tissue) from an oximetry measurement. Thereafter, temperature control logic circuit 2010 may implement different temperature control logic than described above. The system unit may display the splash screen for a period of time (e.g., 10 minutes) or until the minimum number of "in tolerance" measurements have accumulated in the buffer to prevent the system unit from displaying a high-temperature error while the device is overshooting during warm up.

Determining when to display oximetry information during normal operation. The temperature tolerance envelope for displaying valid oximetry measurement information on the display is about + or −0.1 degrees Celsius about the setpoint temperature, in an embodiment. In an alternative embodiment, the temperature tolerance envelope for displaying valid oximetry measurement information on the display is about + or −0.5 degrees Celsius about the setpoint temperature.

Figure 24:
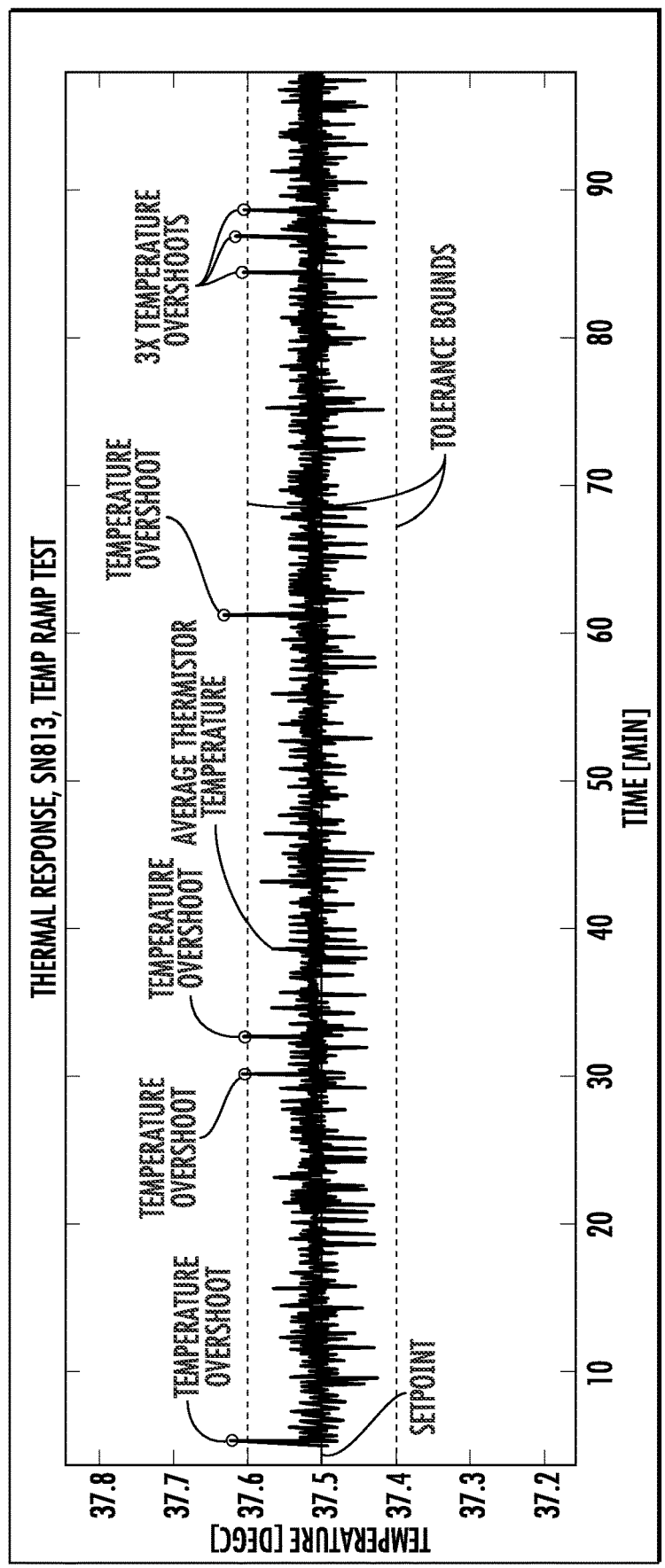
FIG. 24 shows the average temperature sensor detected temperature after the system unit has thermally stabilized.

Occasionally, the reported temperature of the system unit falls outside the tolerance envelope of the setpoint temperature for a single oximetry measurement cycle, even when the temperature of the device is not actually changing. FIG. 24 shows the average temperature sensor detected temperature after the system unit has thermally stabilized. The figure shows a number of cycles when the system unit detects high temperatures for single oximetry measurement cycles above the high tolerance bound of the setpoint temperature.

In an embodiment, the system unit during normal operation, when the in temperature range flag is set, the system unit will continue to display oximetry information for oximetry measurements for these single cycle out of tolerance bounds measurements. The system unit includes a buffer that contains a number (e.g., three) most recently recorded temperatures. The system unit will report a high-low temperature error if all entries (e.g., 3) in the butter are outside of the tolerance bounds. If the system unit reports a high-low temperature error based on the buffer having the number (e.g., 3) of out of tolerance bound temperature measurements during oximetry measurement cycles, the system unit continues to display the error message until all entries (e.g., 3) in the butter are inside of the tolerance bounds.

The system unit will display a high-temperature error message if the system unit is not displaying measured oximetry information and if the buffer has the number (e.g., 3) of out of tolerance bound temperature measurements during oximetry measurement cycles. The system will display a low-temperature error message if the most recent temperature measurement is below the tolerance bound setpoint and if the buffer has the number (e.g., 3) of out of tolerance bound temperature measurements during oximetry measurement cycles.

Setting the size of this buffer is a tradeoff between maximizing sensitivity to actual temperature excursions above and below the temperature bounds of the setpoint temperature, and lowering the lag time after recovery from actual temperature excursions. A buffer size of 3 is a compromise between these considerations.

Table B below includes a pseudocode representation of PI logic of the PI control loop of the temperature control logic circuit. Table B also includes settings that may be used by the pseudocode.

TABLE B

```
Pseudocode Setting:
Tset = 37.5; %setpoint temp, degC
kP = 1.5; %proportional gain
kI = 0.0635; %integral gain
Imax = 1.5; %Integrator Saturation, degC
Lc = 1.2; %adjustment factor
Ierror = 0; %accumulator
t_temp_max = 1.67; %max temp period length
Pseudocode Representation of PI Logic:
%%Control Loop
    %produce error signal
    error = Tset − Tactual;
    %Accumulate error only when within saturation limit
    if abs(Ierror + error)<Imax
    Ierror = Ierror + error;
    end
    %calculate and sum control signals
    control_signal = kP*error + kI*Ierror;
    %adjust magnitude of control signal if we are trying to cool
    if error<0
    control_signal = control_signal*Lc;
    end
    %saturate to maximum length of temp control period
    if control_signal>t_temp_max
    control_signal= t_temp_max;
    end
    if control_signal<−t_temp_max
    control_signal =−t_temp_max;
    end
    %convert control signal into t_temp_on and t_temp_off
    t_temp_on = 0;
    t_temp_off = 0;
    if control_signal>0
    t_temp_on = control_signal;
```

TABLE B-continued

```
    elseif control_signal<0
    t_temp_off = control_signal;
    end
%%end Control Loop
```

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method comprising:
powering on an oximeter device;
detecting a temperature of the oximeter device using a temperature sensor of the oximeter device;
receiving temperature information from the temperature sensor by a processor of the oximeter device;
determining, by the processor, a temperature of the oximeter device based on the temperature information;
determining a temperature difference between the temperature and a temperature setpoint for the oximeter device;
generating a first gain signal that is proportional to the temperature difference;
generating a control signal based on the first gain signal;
generating a second gain signal that is an integral of the temperature difference over time, wherein generating the control signal comprises generating the control signal based on the first and second gain signals and generating the control signal comprises generating the control signal based on a sum of the first and second gain signals;
adjusting the control signal by a gain adjustment factor if the temperature difference is negative;
modulating power supplied to a first light emitting diode (LED) of the oximeter device, using the control signal, to drive the temperature of the oximeter device to the temperature setpoint;
illuminating tissue with light emitted from the first LED;
detecting the light emitted from the first LED by a plurality of photodetectors; and
determining oximetry information for the tissue based on the detected light.

2. The method of claim 1 wherein adjusting the control signal by the gain adjustment factor if the temperature difference is negative comprises multiplying the control signal by the gain adjustment factor if the temperature difference is negative.

3. The method of claim 1 comprising:
if the temperature is below the temperature setpoint for the oximeter device, cooling the device by not supplying power to the LED of the oximeter device to cool the temperature of the oximeter device to the temperature setpoint.

4. The method of claim 3 comprising modulating power supplied to a second LED of the oximeter device if the temperature is above a temperature setpoint for the oximeter device, and using the control signal, to drive the temperature of the oximeter device to the temperature setpoint.

5. The method of claim 4 comprising determining a temperature difference between the temperature and a temperature setpoint for the oximeter device, and modulating power supplied to the second LED based on the temperature difference.

6. The method of claim 5 comprising generating a control signal based on the temperature difference, and using the control signal to modulate the power.

7. The method of claim 6 comprising accumulating the integral of the temperature difference up to a predetermined value.

8. The method of claim 6 comprising not modulating the power supplied to the first LED for warming or cooling the oximeter device if the temperature difference is above or below the temperature setpoint for a single oximetry measurement cycle.

9. The method of claim 1 wherein modulating the power supplied to the first LED of the oximeter device comprises modulating a duty cycle of the power supplied to the first LED of the oximeter device.

10. The method of claim 9 wherein the duty cycle provides the power less than 50 percent of a time per cycle of the power.

11. A method comprising:
powering on an oximeter device;
detecting a temperature of the oximeter device using a temperature sensor of the oximeter device;
receiving temperature information from the temperature sensor by a processor of the oximeter device;
determining, by the processor, a temperature of the oximeter device based on the temperature information;
determining a temperature difference between the temperature and a temperature setpoint for the oximeter device;
generating a first gain signal that is proportional to the temperature difference;
generating a control signal based on the first gain signal;
generating a second gain signal that is an integral of the temperature difference over time;
accumulating the integral of the temperature difference up to a predetermined value;
wherein generating the control signal comprises generating the control signal based on the first and second gain signals;
modulating power supplied to a first light emitting diode (LED) of the oximeter device, using the control signal, to drive the temperature of the oximeter device to the temperature setpoint;
illuminating tissue with light emitted from the first LED;
detecting the light emitted from the first LED by a plurality of photodetectors; and
determining oximetry information for the tissue based on the detected light.

12. The method of claim 11 comprising not modulating the power supplied to the first LED for warming or cooling the oximeter device if the temperature difference is above or below the temperature setpoint for a single oximetry measurement cycle.

13. The method of claim 11 wherein the temperature setpoint comprises a temperature and an upper tolerance temperature that is above the temperature and a lower tolerance temperature that is below the temperature.

14. The method of claim 13 wherein the upper tolerance temperature is above the temperature by one degree Celsius or less, and wherein the lower tolerance temperature that is below the temperature by less than one degree Celsius.

15. The method of claim 11 comprising modulating power supplied to a second LED of the oximeter device, using the control signal, to drive the temperature of the oximeter device to the temperature setpoint;
illuminating tissue with light emitted from the second LED;
detecting the light emitted from the second LED by a plurality of photodetectors; and
determining oximetry information for the tissue based on the detected light.

16. The method of claim 15 wherein modulating power supplied to the second LED is subsequent to modulating power supplied to the first LED.

17. The method of claim 16 comprising modulating power supplied to a third LED of the oximeter device, using the control signal, to drive the temperature of the oximeter device to the temperature setpoint;
illuminating tissue with light emitted from the third LED;
detecting the light emitted from the third LED by a plurality of photodetectors; and
determining oximetry information for the tissue based on the detected light.

18. The method of claim 17 wherein modulating power supplied to the third LED is subsequent to modulating power supplied to the second LED.

19. The method of claim 11 comprising not modulating the power supplied to the first LED for cooling the oximeter device if the temperature difference is above the temperature setpoint for a single oximetry measurement cycle.

20. The method of claim 11 wherein modulating the power supplied to the first LED of the oximeter device comprises modulating a duty cycle of the power supplied to the first LED of the oximeter device.

21. The method of claim 20 wherein the duty cycle provides the power less than 50 percent of a time per cycle of the power.

22. A method comprising:
powering on an oximeter device;
detecting a temperature of the oximeter device using a temperature sensor of the oximeter device;
receiving temperature information from the temperature sensor by a processor of the oximeter device;
determining, by the processor, a temperature of the oximeter device based on the temperature information;
if the temperature is below a temperature setpoint for the oximeter device, cooling the device by not supplying power to a first light emitting diode (LED) of the oximeter device to cool the temperature of the oximeter device to the temperature setpoint;
determining a temperature difference between the temperature and a temperature setpoint for the oximeter device;
generating a control signal based on the temperature difference, and using the control signal to modulate the power;
modulating power supplied to the LED based on the control signal for the temperature difference if the temperature different is above a temperature setpoint difference for the oximeter device;
using the control signal, to drive the temperature of the oximeter device to the temperature setpoint;
generating a first gain signal that is proportional to the temperature difference, wherein generating the control signal comprises generating the control signal based on the first gain signal;
generating a second gain signal that is an integral of the temperature difference over time, wherein generating the control signal comprises generating the control signal based on the first and second gain signals, wherein generating the control signal comprises generating the control signal based on a sum of the first and second gain signals; and adjusting the control signal by a gain adjustment factor if the temperature difference is negative;

illuminating tissue with light emitted from the first LED;

detecting the light emitted from the first LED by a plurality of photodetectors; and determining oximetry information for the tissue based on the detected light.

23. The method of claim 22 comprising accumulating the integral of the temperature difference up to a predetermined value.

24. The method of claim 22 wherein adjusting the control signal by the gain adjustment factor if the temperature difference is negative comprises multiplying the control signal by the gain adjustment factor if the temperature difference is negative.

25. The method of claim 22 comprising providing for the control signal to be used to modulate a duty cycle of the power supplied to the first LED of the oximeter device.

26. The method of claim 25 wherein the duty cycle provides the power less than 50 percent of a time per cycle of the power.

27. A method comprising:
powering on an oximeter device;
detecting a temperature of the oximeter device using a temperature sensor of the oximeter device;
receiving temperature information from the temperature sensor by a processor of the oximeter device;
determining, by the processor, a temperature of the oximeter device based on the temperature information;
if the temperature is below a temperature setpoint for the oximeter device, cooling the device by not supplying power to a first light emitting diode (LED) of the oximeter device to cool the temperature of the oximeter device to the temperature setpoint;
determining a temperature difference between the temperature and a temperature setpoint for the oximeter device;
modulating power supplied to the LED based on the control signal for the temperature difference if the temperature is above a temperature setpoint difference for the oximeter device;
using the control signal, to drive the temperature of the oximeter device to the temperature setpoint;
generating a control signal based on the temperature difference, and using the control signal to modulate the power;
generating a first gain signal that is proportional to the temperature difference, wherein generating the control signal comprises generating the control signal based on the first gain signal;
generating a second gain signal that is an integral of the temperature difference over time, wherein generating the control signal comprises generating the control signal based on the first and second gain signals;
accumulating the integral of the temperature difference up to a predetermined value;
illuminating tissue with light emitted from the first LED;
detecting the light emitted from the first LED by a plurality of photodetectors; and
determining oximetry information for the tissue based on the detected light.

28. The method of claim 27 comprising providing for the control signal to be used to modulate a duty cycle of the power supplied to the first LED of the oximeter device.

29. The method of claim 28 wherein the duty cycle provides the power less than 50 percent of a time per cycle of the power.

30. A method comprising:
powering on an oximeter device;
detecting a temperature of the oximeter device using a temperature sensor of the oximeter device;
receiving temperature information from the temperature sensor by a processor of the oximeter device;
determining, by the processor, a temperature of the oximeter device based on the temperature information;
determining a temperature difference between the temperature and a temperature setpoint for the oximeter device;
if the temperature is below a temperature setpoint for the oximeter device, cooling the device by not supplying power to a first light emitting diode (LED) of the oximeter device to cool the temperature of the oximeter device to the temperature setpoint;
modulating power supplied to the first LED of the oximeter device if the temperature is above a temperature setpoint for the oximeter device and based on the temperature difference
generating a first gain signal that is proportional to the temperature difference;
generating a second gain signal that is an integral of the temperature difference over time;
accumulating the integral of the temperature difference up to a predetermined value;
generating a control signal based on the first and second gain signals;
using the control signal to modulate the power to drive the temperature of the oximeter device to the temperature setpoint;
illuminating tissue with light emitted from the first LED;
detecting the light emitted from the first LED by a plurality of photodetectors; and
determining oximetry information for the tissue based on the detected light.

31. The method of claim 30 wherein the temperature setpoint comprises a temperature and an upper tolerance temperature that is above the temperature and a lower tolerance temperature that is below the temperature.

32. The method of claim 31 wherein the upper tolerance temperature is above the temperature by one degree Celsius or less, and wherein the lower tolerance temperature that is below the temperature by less than one degree Celsius.

33. The method of claim 30 comprising modulating power supplied to a second LED of the oximeter device, using the control signal, to drive the temperature of the oximeter device to the temperature setpoint;
illuminating tissue with light emitted from the second LED;
detecting the light emitted from the second LED by a plurality of photodetectors; and
determining oximetry information for the tissue based on the detected light.

34. The method of claim 33 wherein modulating power supplied to the second LED is subsequent to modulating power supplied to the first LED.

35. The method of claim 34 comprising modulating power supplied to a third LED of the oximeter device, using the control signal, to drive the temperature of the oximeter device to the temperature setpoint;

illuminating tissue with light emitted from the third LED;
detecting the light emitted from the third LED by a plurality of photodetectors; and
determining oximetry information for the tissue based on the detected light.

36. The method of claim 35 wherein modulating power supplied to the third LED is subsequent to modulating power supplied to the second LED.

37. A method comprising:
powering on an oximeter device;
detecting a temperature of the oximeter device using a temperature sensor of the oximeter device;
receiving temperature information from the temperature sensor by a processor of the oximeter device;
determining, by the processor, a temperature of the oximeter device based on the temperature information;
determining a temperature difference between the temperature and a temperature setpoint for the oximeter device;
generating a first gain signal that is proportional to the temperature difference;
generating a second gain signal that is an integral of the temperature difference over time;
accumulating the integral of the temperature difference up to a predetermined value;
generating a control signal based on the first and second gain signals;
modulating power supplied to a first light emitting diode (LED) of the oximeter device, using the control signal, to drive the temperature of the oximeter device to the temperature setpoint;
illuminating tissue with light emitted from the first LED;
detecting the light emitted from the first LED by a plurality of photodetectors; and
determining oximetry information for the tissue based on the detected light.

38. The method of claim 37 wherein the modulating the power supplied to the first LED of the oximeter device comprises altering a duty cycle of the power supplied to the first LED of the oximeter device.

39. The method of claim 38 wherein the duty cycle provides the power less than 50 percent of a time per cycle of the power.

40. A method comprising:
powering on an oximeter device;
detecting a temperature of the oximeter device using a temperature sensor of the oximeter device;
receiving temperature information from the temperature sensor by a processor of the oximeter device;
determining, by the processor, a temperature of the oximeter device based on the temperature information;
determining a temperature difference between the temperature and a temperature setpoint for the oximeter device;
generating a first gain signal that is proportional to the temperature difference;
generating a second gain signal that is an integral of the temperature difference over time;
accumulating the integral of the temperature difference up to a predetermined value;
generating a control signal based on a sum of the first and second gain signals;
adjusting the control signal by a gain adjustment factor if the temperature difference is negative;
modulating power supplied to a first light emitting diode (LED) of the oximeter device, using the control signal, to drive the temperature of the oximeter device to the temperature setpoint;
illuminating tissue with light emitted from the first LED;
detecting the light emitted from the first LED by a plurality of photodetectors; and
determining oximetry information for the tissue based on the detected light.

41. The method of claim 40 wherein adjusting the control signal by the gain adjustment factor if the temperature difference is negative comprises multiplying the control signal by the gain adjustment factor if the temperature difference is negative.

42. A method comprising:
powering on an oximeter device;
detecting a temperature of the oximeter device using a temperature sensor of the oximeter device;
receiving temperature information from the temperature sensor by a processor of the oximeter device;
determining, by the processor, a temperature of the oximeter device based on the temperature information;
determining a temperature difference between the temperature and a temperature setpoint for the oximeter device;
if the temperature is below a temperature setpoint for the oximeter device, cooling the device by not supplying power to a first light emitting diode (LED) of the oximeter device to cool the temperature of the oximeter device to the temperature setpoint;
modulating power supplied to the first LED of the oximeter device if the temperature is above a temperature setpoint for the oximeter device and based on the temperature difference
generating a first gain signal that is proportional to the temperature difference;
generating a second gain signal that is an integral of the temperature difference over time;
generating a control signal based on a sum of the first and second gain signals;
adjusting the control signal by a gain adjustment factor if the temperature difference is negative;
using the control signal to modulate the power to drive the temperature of the oximeter device to the temperature setpoint;
illuminating tissue with light emitted from the first LED;
detecting the light emitted from the first LED by a plurality of photodetectors; and
determining oximetry information for the tissue based on the detected light.

43. The method of claim 42 wherein adjusting the control signal by the gain adjustment factor if the temperature difference is negative comprises multiplying the control signal by the gain adjustment factor if the temperature difference is negative.

* * * * *